United States Patent
Norton et al.

(10) Patent No.: US 10,729,746 B2
(45) Date of Patent: Aug. 4, 2020

(54) RECOMBINANT PLACENTA GROWTH FACTOR FOR TREATING DUCHENNE MUSCULAR DYSTROPHY

(71) Applicant: Shire Human Genetic Therapies, Inc., Lexington, MA (US)

(72) Inventors: Angela Norton, Lexington, MA (US); Michael F. Concino, Lexington, MA (US); Muthuraman Meiyappan, Lexington, MA (US); Andrea Iskenderian, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 14/763,783

(22) PCT Filed: Jan. 28, 2014

(86) PCT No.: PCT/US2014/013396
§ 371 (c)(1),
(2) Date: Jul. 27, 2015

(87) PCT Pub. No.: WO2014/117155
PCT Pub. Date: Jul. 31, 2014

(65) Prior Publication Data
US 2015/0368309 A1    Dec. 24, 2015

Related U.S. Application Data

(60) Provisional application No. 61/757,569, filed on Jan. 28, 2013.

(51) Int. Cl.
| | | |
|---|---|---|
| *A61K 38/18* | (2006.01) | |
| *C07K 14/475* | (2006.01) | |
| *C07K 14/515* | (2006.01) | |

(52) U.S. Cl.
CPC .......... *A61K 38/18* (2013.01); *A61K 38/1866* (2013.01); *C07K 14/475* (2013.01); *C07K 14/515* (2013.01); *C07K 2319/00* (2013.01)

(58) Field of Classification Search
None
See application file for complete search history.

(56) References Cited

U.S. PATENT DOCUMENTS

2015/0361174 A1   12/2015  Josiah et al.

FOREIGN PATENT DOCUMENTS

| WO | WO 01/056593 A2 * | 8/2001 |
|---|---|---|
| WO | WO-03/066676 A1 | 8/2003 |
| WO | WO-03/074075 A1 | 9/2003 |
| WO | WO-2006/055809 A2 | 5/2006 |
| WO | WO-2011/029861 A1 | 3/2011 |
| WO | WO-2014/117160 A1 | 7/2014 |

OTHER PUBLICATIONS

Cebe-Suarez et al. Cell. Mol. Life Sci. 63: 601-15, 2006.*
Shibuya Angiogenesis 9: 225-230, 2006.*
Gadhann et al. Am. J. Physiol. Heart Circ. Physiol. 286: H152-H164, 2004.*
Lutton et al. Nat. Med 8: 831-840, 2002.*
Saito et al. (Brain Develop. 31: 612-617, 2009).*
Altschul et al., Basic Local Alignment Search Tool, J. Mol. Biol., 215(3):403-410 (1990).
Altschul et al., Gapped BLAST and PSI-BLAST: a new generation of protein database search programs, Nucleic Acids Res., 25(17):3389-3402 (1997).
Baxevanis et al., Bioinformatics: A Practical Guide to the Analysis of Genes and Proteins, Wiley (1998).
Boesen, T. et al., Single-chain vascular endothelial growth factor variant with antagonist activity, The Journal of Biological Chemistry, 277(43):40335-40341 (2002).
Ennen, J. P. et al., Vascular-targeted therapies for Duchenne muscular dystrophy, Skeletal Muscle, 3:9 (2013).
Errico, M. et al., Identification of Placenta Growth Factor Determinants for Binding and Activation of Flt-1 Receptor, The Journal of Biological Chemistry, 279:43929-43939 (2004).
Gargioli, C. et al., P1GF-MMP-9-expressing cells restore microcirculation and efficacy of cell therapy in aged dystrophic muscle, Nature Medicine, 14(9):973-978 (2008).
Graham et al., Characteristics of a Human Cell Line Transformed by DNA from Human Adenovirus Type 5, J. Gen Virol., 36:59-72 (1977).
International Search Report for PCT/US2014/013396, 4 pages (dated May 22, 2014).
International Search Report for PCT/US2014/013402, dated Jul. 2, 2014, 6 pages.
Mather et al., Culture of Testicular Cells in Hormone-Supplemented Serum-Free Medium, Annals New York Acad. Sci., 383:44-68 (1982).
Mather, Establishment and characterization of two distinct mouse testicular epithelial cell lines, Biol. Reprod., 23: 243-251, 1980.
Messina, S. et al., VEGF overexpression via adeno-associated virus gene transfer promotes skeletal muscle regeneration and enhances muscle function in mdx mice, The FASEB Journal, 21:3737-3746 (2007).

(Continued)

Primary Examiner — Christine J Saoud
(74) Attorney, Agent, or Firm — Proskauer Rose LLP; Fangli Chen; Julio J. Mendez

(57) ABSTRACT

The present invention provides, among other things, methods and compositions for treating muscular dystrophy, in particular, Duchenne muscular dystrophy (DMD). In some embodiments, a method according to the present invention includes administering to an individual who is suffering from or susceptible to DMD an effective amount of a recombinant PLGF protein such that at least one symptom or feature of DMD is reduced in intensity, severity, or frequency, or has delayed onset. The present invention also provides exemplary recombinant PLGF proteins including monomeric, dimeric and single-chain PLGF proteins.

15 Claims, 6 Drawing Sheets

Specification includes a Sequence Listing.

(56) References Cited

OTHER PUBLICATIONS

Misener, S. and Krawetz, S., Bioinformatics Methods and Protocols, Methods in Molecular Biology, 132, Humana Press (1999).
Sanz, L. et al., Antibodies and gene therapy: teaching old 'magic bullets' new tricks, Trends in Immunology, 25(2):85-91 (2004).
Shimizu-Motohashi, Y. and Asakura, A., Angiogenesis as a novel therapeutic strategy for Duchenne muscular dystrophy through decreased ischemia and increased satellite cells, Frontiers in Physiology, 5(50)1-17 (2014).
Urlaub and Chasin, Isolation of Chinese hamster cell mutants deficient in dihydrofolate reductase activity, Proc. Natl. Acad. Sci. USA, 77(7): 4216-4220, 1980.
Verma, M. et al., Flt-1 haploinsufficiency ameliorates muscular dystrophy phenotype by developmentally increased vasculature in mdx mice, Human Molecular Genetics, 19:(21) (2010).
Written Opinion for PCT/US2014/013396, 9 pages (dated May 22, 2014).
Wu, Y. et al., Anti-Vascular Endothelial Growth Factor Receptor-1 Antagonist Antibody as a Therapeutic Agent for Cancer, Clin. Cancer Res 12:(21):6573-6584 (2006).

\* cited by examiner

SEQUENCE LISTING

```
<160> NUMBER OF SEQ ID NOS: 22

<210> SEQ ID NO 1
<211> LENGTH: 131
<212> TYPE: PRT
<213> ORGANISM: Homo sapiens

<400> SEQUENCE: 1

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 2
<211> LENGTH: 131
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Ala Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 3
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg Gly Ser Thr Ser Gly Ser Gly Lys Ser Ser Glu Gly Lys
    130                 135                 140

Gly Pro Ala Val Pro Pro Gln Gln Trp Ala Leu Ser Ala Gly Asn Gly
145                 150                 155                 160

Ser Ser Glu Val Glu Val Val Pro Phe Gln Glu Val Trp Gly Arg Ser
            165                 170                 175

Tyr Cys Arg Ala Leu Glu Arg Leu Val Asp Val Val Ser Glu Tyr Pro
                180                 185                 190

Ser Glu Val Glu His Met Phe Ser Pro Ser Cys Val Ser Leu Leu Arg
            195                 200                 205

Cys Thr Gly Cys Cys Gly Asp Glu Asn Leu His Cys Val Pro Val Glu
        210                 215                 220

Thr Ala Asn Val Thr Met Gln Leu Leu Lys Ile Arg Ser Gly Asp Arg
225                 230                 235                 240

Pro Ser Tyr Val Glu Leu Thr Phe Ser Gln His Val Arg Cys Glu Cys
                245                 250                 255

Arg Pro Leu Arg Glu Lys Met Lys Pro Glu Arg Cys Gly Asp Ala Val
            260                 265                 270

Pro Arg Arg
        275

<210> SEQ ID NO 4
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg Gly Ser Thr Ser Gly Ser Gly Lys Ser Ser Glu Gly Lys
    130                 135                 140

Gly Pro Ala Val Pro Pro Gln Gln Trp Ala Leu Ser Ala Gly Asn Gly
145                 150                 155                 160

Ser Ser Glu Val Glu Val Val Pro Phe Gln Glu Val Trp Gly Arg Ser
                165                 170                 175

Tyr Cys Arg Ala Leu Glu Arg Leu Val Asp Val Val Ser Glu Tyr Pro
            180                 185                 190

Ser Glu Val Glu His Met Phe Ser Pro Ser Cys Val Ser Leu Leu Arg
        195                 200                 205

Cys Thr Gly Cys Cys Gly Ala Ala Asn Leu His Cys Val Pro Val Glu
    210                 215                 220

Thr Ala Asn Val Thr Met Gln Leu Leu Lys Ile Arg Ser Gly Asp Arg
225                 230                 235                 240

```
Pro Ser Tyr Val Glu Leu Thr Phe Ser Gln His Val Arg Cys Glu Cys
            245                 250                 255

Arg Pro Leu Arg Glu Lys Met Lys Pro Glu Arg Cys Gly Asp Ala Val
        260                 265                 270

Pro Arg Arg
    275

<210> SEQ ID NO 5
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg Gly Ser Thr Ser Gly Ser Gly Lys Ser Ser Glu Gly Lys
    130                 135                 140

Gly Pro Ala Val Pro Pro Gln Gln Trp Ala Leu Ser Ala Gly Asn Gly
145                 150                 155                 160

Ser Ser Glu Val Glu Val Val Pro Phe Gln Glu Val Trp Gly Arg Ser
            165                 170                 175

Tyr Cys Arg Ala Leu Glu Arg Leu Val Asp Val Val Ser Glu Tyr Pro
        180                 185                 190

Ser Glu Val Glu His Met Phe Ser Pro Ser Cys Val Ser Leu Leu Arg
    195                 200                 205

Cys Thr Gly Cys Cys Gly Ser Ala Asn Leu His Cys Val Pro Val Glu
210                 215                 220

Thr Ala Asn Val Thr Met Gln Leu Leu Lys Ile Arg Ser Gly Asp Arg
225                 230                 235                 240

Pro Ser Tyr Val Glu Leu Thr Phe Ser Gln His Val Arg Cys Glu Cys
            245                 250                 255

Arg Pro Leu Arg Glu Lys Met Lys Pro Glu Arg Cys Gly Asp Ala Val
        260                 265                 270

Pro Arg Arg
    275

<210> SEQ ID NO 6
<211> LENGTH: 275
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Leu Pro Ala Val Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
                35                  40                  45

Ser Glu Val Glu His Met Phe Ser Pro Ser Cys Val Ser Leu Leu Arg
50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
                100                 105                 110

Arg Pro Leu Arg Glu Lys Met Lys Pro Glu Arg Cys Gly Asp Ala Val
            115                 120                 125

Pro Arg Arg Gly Ser Thr Ser Gly Ser Gly Lys Ser Ser Glu Gly Lys
130                 135                 140

Gly Pro Ala Val Pro Pro Gln Gln Trp Ala Leu Ser Ala Gly Asn Gly
145                 150                 155                 160

Ser Ser Glu Val Glu Val Val Pro Phe Ala Glu Val Trp Gly Arg Ser
                165                 170                 175

Tyr Cys Arg Ala Leu Glu Arg Leu Val Asp Val Val Ser Glu Tyr Pro
                180                 185                 190

Ser Glu Val Glu His Met Phe Ser Pro Ser Cys Val Ser Leu Leu Arg
            195                 200                 205

Cys Thr Gly Cys Cys Gly Ser Ala Asn Leu His Cys Val Pro Val Glu
210                 215                 220

Thr Ala Asn Val Thr Met Gln Leu Leu Lys Ile Arg Ser Gly Asp Arg
225                 230                 235                 240

Pro Ser Tyr Val Glu Leu Thr Phe Ser Gln His Val Arg Cys Glu Cys
                245                 250                 255

Arg Pro Leu Arg Glu Lys Met Lys Pro Glu Arg Cys Gly Asp Ala Val
            260                 265                 270

Pro Arg Arg
        275
```

<210> SEQ ID NO 7
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
                20                  25                  30
```

```
Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
 50                      55                  60

Cys Thr Gly Cys Cys Gly Asp Glu Asn Leu His Cys Val Pro Val Glu
 65                  70                  75                  80

Thr Ala Asn Val Thr Met Gln Leu Leu Lys Ile Arg Ser Gly Asp Arg
                 85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
            115                 120                 125

Pro Arg Arg Gly Ser Thr Ser Gly Ser Gly Lys Ser Ser Glu Gly Lys
            130                 135                 140

Gly Pro Ala Val Pro Pro Gln Gln Trp Ala Leu Ser Ala Gly Asn Gly
145                 150                 155                 160

Ser Ser Glu Val Glu Val Val Pro Phe Gln Glu Val Ala Gly Arg Ser
                165                 170                 175

Tyr Cys Arg Ala Leu Glu Arg Leu Val Asp Val Val Ser Glu Tyr Pro
            180                 185                 190

Ser Glu Val Glu His Met Phe Ser Pro Ser Cys Val Ser Leu Leu Arg
            195                 200                 205

Cys Thr Gly Cys Cys Gly Ser Ala Asn Leu His Cys Val Pro Val Glu
            210                 215                 220

Thr Ala Asn Val Thr Met Gln Leu Leu Lys Ile Arg Ser Gly Asp Arg
225                 230                 235                 240

Pro Ser Tyr Val Glu Leu Thr Phe Ser Gln His Val Arg Cys Glu Cys
                245                 250                 255

Arg Pro Leu Arg Glu Lys Met Lys Pro Glu Arg Cys Gly Asp Ala Val
            260                 265                 270

Pro Arg Arg
        275

<210> SEQ ID NO 8
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Leu Pro Ala Val Pro Pro Gln Gln Trp Ala Leu Ser Ala Gly Asn Gly
 1               5                  10                  15

Ser Ser Glu Val Glu Val Val Pro Phe Gln Glu Val Trp Gly Arg Ser
                 20                  25                  30

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
 50                      55                  60

Cys Thr Gly Cys Cys Gly Asp Glu Asn Leu His Cys Val Pro Val Glu
 65                  70                  75                  80

Thr Ala Asn Val Thr Met Gln Leu Leu Lys Ile Arg Ser Gly Asp Arg
                 85                  90                  95
```

```
Pro Ser Tyr Val Glu Leu Thr Phe Ser Gln His Val Arg Cys Glu Cys
                100                 105                 110

Arg Pro Leu Arg Glu Lys Met Lys Pro Glu Arg Cys Gly Asp Ala Val
            115                 120                 125

Pro Arg Arg Gly Ser Thr Ser Gly Ser Gly Lys Ser Ser Glu Gly Lys
        130                 135                 140

Gly Pro Ala Val Pro Pro Gln Gln Trp Ala Leu Ser Ala Gly Asn Gly
145                 150                 155                 160

Ser Ser Glu Val Glu Val Val Pro Phe Gln Glu Val Trp Gly Arg Ser
                165                 170                 175

Tyr Cys Arg Ala Leu Glu Arg Leu Val Asp Val Val Ser Glu Tyr Pro
            180                 185                 190

Ser Glu Val Glu His Met Phe Ser Pro Ser Cys Val Ser Leu Leu Arg
        195                 200                 205

Cys Thr Gly Cys Cys Gly Ser Ala Asn Arg His Cys Val Pro Val Glu
        210                 215                 220

Thr Ala Asn Val Thr Met Gln Leu Leu Lys Ile Arg Ser Gly Asp Arg
225                 230                 235                 240

Pro Ser Tyr Val Glu Leu Thr Phe Ser Gln His Val Arg Cys Glu Cys
                245                 250                 255

Arg Pro Leu Arg Glu Lys Met Lys Pro Glu Arg Cys Gly Asp Ala Val
            260                 265                 270

Pro Arg Arg
        275

<210> SEQ ID NO 9
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
                20                  25                  30

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
        50                  55                  60

Cys Thr Gly Cys Cys Gly Ala Ala Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
        130

<210> SEQ ID NO 10
<211> LENGTH: 131
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Ser Ala Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 11
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Leu Pro Ala Val Pro Pro Gln Gln Trp Ala Leu Ser Ala Gly Asn Gly
1               5                   10                  15

Ser Ser Glu Val Glu Val Val Pro Phe Ala Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Ser Ala Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 12
<211> LENGTH: 131
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 12

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Ala Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Ser Ala Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 13
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Ser Ala Asn Arg His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Cys Gly Asp Ala Val
        115                 120                 125

Pro Arg Arg
    130

<210> SEQ ID NO 14
<211> LENGTH: 14
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 14

Gly Ser Thr Ser Gly Ser Gly Lys Ser Ser Glu Gly Lys Gly
1               5                   10

<210> SEQ ID NO 15
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ala Pro Gly Gly Gly Gly Ala Ala Ala Ala Gly Gly Gly
1               5                   10                  15

Gly Gly Gly Ala Pro
            20

<210> SEQ ID NO 16
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro
            35

<210> SEQ ID NO 17
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro Gly Gly Gly Gly Ala Ala Ala Ala
                35                  40                  45

Ala Gly Gly Gly Gly Gly Gly Ala Pro
    50                  55

<210> SEQ ID NO 18
<211> LENGTH: 232
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 18

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 19
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(5)
<223> OTHER INFORMATION: /replace="Glu" or "Ala" or "Val" or "Leu" or
      "Ile" or "Pro" or "Phe" or "Tyr" or "Trp" or "Ser" or "Thr" or
      "Met" or "Asn" or "Gln" or "Lys" or "Arg" or "His" or
      "Asp"
<220> FEATURE:
<221> NAME/KEY: misc_feature
<222> LOCATION: (1)..(232)
<223> OTHER INFORMATION: /note="Variant residues given in the sequence
      have no preference with respect to those in the annotations
      for variant positions"

<400> SEQUENCE: 19

Glu Pro Lys Ser Gly Asp Lys Thr His Thr Cys Pro Pro Cys Pro Ala
1               5                   10                  15

Pro Glu Leu Leu Gly Gly Pro Ser Val Phe Leu Phe Pro Pro Lys Pro

```
            20                  25                  30
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 20
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 152
<212> TYPE: PRT
<213> ORGANISM: Homo sapiens

<400> SEQUENCE: 21

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Arg Arg Pro Lys Gly
        115                 120                 125

Arg Gly Lys Arg Arg Arg Glu Lys Gln Arg Pro Thr Asp Cys His Leu
    130                 135                 140

Cys Gly Asp Ala Val Pro Arg Arg
145                 150

<210> SEQ ID NO 22
<211> LENGTH: 203
<212> TYPE: PRT
<213> ORGANISM: Homo sapiens

<400> SEQUENCE: 22

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80
```

```
Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg His Ser Pro Gly Arg Gln Ser Pro Asp Met Pro Gly Asp Phe Arg
        115                 120                 125

Ala Asp Ala Pro Ser Phe Leu Pro Pro Arg Arg Ser Leu Pro Met Leu
    130                 135                 140

Phe Arg Met Glu Trp Gly Cys Ala Leu Thr Gly Ser Gln Ser Ala Val
145             150                 155                 160

Trp Pro Ser Ser Pro Val Pro Glu Glu Ile Pro Arg Met His Pro Gly
                165                 170                 175

Arg Asn Gly Lys Lys Gln Gln Arg Lys Pro Leu Arg Glu Lys Met Lys
            180                 185                 190

Pro Glu Arg Cys Gly Asp Ala Val Pro Arg Arg
        195                 200
```

RECOMBINANT PLACENTA GROWTH FACTOR FOR TREATING DUCHENNE MUSCULAR DYSTROPHY

CROSS-REFERENCE TO RELATED APPLICATIONS

The present application is a U.S. National Stage Application filed under 35 U.S.C. § 371 based on International Application No. PCT/US2014/013396, filed Jan. 28, 2014, which claims priority to U.S. Provisional Application Ser. No. 61/757,569 filed Jan. 28, 2013, the disclosure of each of which is incorporated herein by reference in their entirety.

BACKGROUND

Duchenne muscular dystrophy (DMD) is a recessive X-linked form of muscular dystrophy, affecting around 1 in 3,600 boys, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemnal membrane function. While both sexes can carry the mutation, females rarely exhibit typical clinical features of the disease seen in boys.

Presently, there is no known cure for DMD. Several therapeutic avenues have been investigated including gene therapy and administration of corticosteroids. While some of these treatments may delay certain symptoms, there is presently no satisfactory therapeutic option for DMD patients.

SUMMARY OF THE INVENTION

The present invention provides, among other things, improved methods and compositions for treating muscular dystrophy, in particular, Duchenne muscular dystrophy (DMD) and/or Becker Muscular Dystrophy based on placenta growth factor (PLGF) therapy. The invention is, in part, based on the discovery that PLGF, including single-chain PLGF, can inhibit VEGF and other ligands from binding to Flt-1 binding sites and/or Flt-1 receptors, thereby increasing the amount of VEGF and/or other ligands available to bind to additional functional VEGF receptors (e.g. VEGF 2 (Flk-1)), resulting in improvements in DMD symptoms.

In some embodiments, the present invention provides methods of treating Duchenne Muscular Dystrophy (DMD) comprising administering to an individual who is suffering from or susceptible to DMD an effective amount of a recombinant placenta growth factor (PLGF) protein such that at least one symptom or feature of DMD is reduced in intensity, severity, or frequency, or has delayed onset.

In some embodiments, the recombinant placenta growth factor (PLGF) protein is a single-chain PLGF protein.

In some embodiments, the single-chain PLGF protein is a monomeric PLGF protein comprising an amino acid sequence at least 70%, 80%, 90% or 95% identical to the wild-type human PLGF protein (SEQ ID NO: 1) and amino acid substitution of Ala for Cys at a position corresponding to position 59 of the full-length PLGF as shown below.

(SEQ ID NO: 1)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRR.

In some embodiments, the monomeric PLGF protein comprises the amino acid sequence as shown in SEQ ID NO: 2 (which is otherwise identical to the wild-type human PLGF protein except amino acid substitution of Ala for Cys at position 59 of the mature full-length human PLGF) as shown below.

(SEQ ID NO: 2)
LPAVPPQQWALSAGNGSSEVEVVPFQEVWGRSYCRALERLVDVVSEYPSE

VEHMFSPSAVSLLRCTGCCGDENLHCVPVETANVTMQLLKIRSGDRPSYV

ELTFSQHVRCECRPLREKMKPERCGDAVPRR.

In some embodiments, a monomeric PLGF protein comprises one or more additional deletions, mutations or insertions as compared to the wild-type human PLGF protein.

In some embodiments, a single-chain PLGF protein comprises two fused PLGF monomers.

In some embodiments, each of the two fused monomers comprises an amino acid sequence at least 70%, 80%, 90%, or 95% identical to the wild-type human PLGF protein (SEQ ID NO: 1).

In some embodiments, at least one of the two fused monomers is a wild-type human PLGF monomer.

In some embodiments, at least one of the two fused monomers comprises one or more mutations at positions selected from the group consisting of Q26, W29, D71, E72, L74, and combinations thereof. In some embodiments, one or more mutations are selected from the group consisting of Q26A, W29A, D71A, D71S, E72A, L74R, and combinations thereof.

In some embodiments, the N-terminal monomer is a wild-type PLGF monomer and the C-terminal monomer comprises the one or more mutations.

In some embodiments, the C-terminal monomer is a wild-type PLGF monomer and the N-terminal monomer comprises one or more mutations.

In some embodiments, two monomers are fused via a linker.

In some embodiments, the linker is a peptide. In some embodiments, the linker is a peptide comprising 3-60 amino acids (e.g., 3-55, 3-50, 3-45, 3-40, 3-35, 3-30, 3-25, 3-20, 3-15, or 3-10 amino acids).

In some embodiments, the linker comprises a sequence that is at least 80%, 85%, 90%, or 95% identical to GST-SGSGKSSEGKG (SEQ ID NO: 14).

In some embodiments, the linker comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGGAP (SEQ ID NO: 15) (GAG linker). In some embodiments, the linker comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGGAP (SEQ ID NO: 16) (GAG2 linker). In some embodiments, the linker comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGG
GAPGGGGGAAAAAGGGGG GAP (SEQ ID NO: 17) (GAG3 linker).

In some embodiments, the single-chain PLGF protein has amino acid sequence selected from the group consisting of:

```
(Wild type fusion)
                                     (SEQ ID NO: 3)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRRGSTSGSGKSSEGKGPAVPP

QQWALSAGNGSSEVEVVPFQEVWGRSYCRALERLVDVVSEYPSEVEHMFS

PSCVSLLRCTGCCGDENLHCVPVETANVTMQLLKIRSGDRPSYVELTFSQ

HVRCECRPLREKMKPERCGDAVPRR, (scPLGF-D71A/E72A of PLGF, mutations
corresponding to positionsD215A/E216A of PLGF
mutant fused to wild-type PLGF via 14 aa linker)
                                     (SEQ ID NO: 4)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRRGSTSGSGKSSEGKGPAVPP

QQWALSAGNGSSEVEVVPFQEVWGRSYCRALERLVDVVSEYPSEVEHMFS

PSCVSLLRCTGCCGAANLHCVPVETANVTMQLLKIRSGDRPSYVELTFSQ

HVRCECRPLREKMKPERCGDAVPRR, (scPLGF-D71S/E72A of PLGF, mutations
corresponding to positionsD215S/E216A of PLGF
mutant fused to wild-type PLGF via 14 aa linker)
                                     (SEQ ID NO: 5)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRRGSTSGSGKSSEGKGPAVPP

QQWALSAGNGSSEVEVVPFQEVWGRSYCRALERLVDVVSEYPSEVEHMFS

PSCVSLLRCTGCCGSANLHCVPVETANVTMQLLKIRSGDRPSYVELTFSQ

HVRCECRPLREKMKPERCGDAVPRR, (scPLGF-Q26A/D71S/E72A of PLGF, mutations
corresponding to positionsQ170A/D215S/E216A of
PLGF mutant fused to wild-type PLGF via 14 aa
linker)
                                     (SEQ ID NO: 6)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRRGSTSGSGKSSEGKGPAVPP

QQWALSAGNGSSEVEVVPFAEVWGRSYCRALERLVDVVSEYPSEVEHMFS

PSCVSLLRCTGCCGSANLHCVPVETANVTMQLLKIRSGDRPSYVELTFSQ

HVRCECRPLREKMKPERCGDAVPRR, (scPLGF-W29A/D71S/E72A of PLGF, mutations
corresponding to positionsW173A/D215S/E216A
of PLGF mutant fused to wild-type PLGF via
14 aa linker)
                                     (SEQ ID NO: 7)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRRGSTSGSGKSSEGKGPAVPP

-continued
QQWALSAGNGSSEVEVVPFQEVAGRSYCRALERLVDVVSEYPSEVEHMFS

PSCVSLLRCTGCCGSANLHCVPVETANVTMQLLKIRSGDRPSYVELTFSQ

HVRCECRPLREKMKPERCGDAVPRR,
and (scPLGF-D71S/E72A/L74R PLGF, mutations
corresponding to positionsD215S/E216A/L218R of
PLGF mutant fused to wild-type PLGF via 14 aa
linker)
                                     (SEQ ID NO: 8)
LPAVPPQQWALSAGNGSSEVEVVPFQEVWGRSYCRALERLVDVVSEYPSE

VEHMFSPSCVSLLRCTGCCGDENLHCVPVETANVTMQLLKIRSGDRPSYV

ELTFSQHVRCECRPLREKMKPERCGDAVPRRGSTSGSGKSSEGKGPAVPP

QQWALSAGNGSSEVEVVPFQEVWGRSYCRALERLVDVVSEYPSEVEHMFS

PSCVSLLRCTGCCGSANRHCVPVETANVTMQLLKIRSGDRPSYVELTFSQ

HVRCECRPLREKMKPERCGDAVPRR.
```

In some embodiments, the recombinant placenta growth factor (PLGF) protein is a dimeric PLGF protein comprising two monomers.

In some embodiments, each of the two monomers comprises an amino acid sequence at least 70%, 80%, 85%, 90% or 95% identical to the wild-type human PLGF protein (SEQ ID NO: 1).

In some embodiments, at least one of the two monomers is a wild-type human PLGF monomer. In some embodiments, the recombinant PLGF protein is the wild-type human PLGF protein (SEQ ID NO: 1).

In some embodiments, recombinant PLGF protein is produced from mammalian cells. In some embodiments, the mammalian cells are human cells. In some embodiments, the mammalian cells are Chinese Hamster Ovary (CHO) cells. In some embodiments, the mammalian cells are human cells. In some embodiments, the mammalian cells are Human Embryonic Kidney (HEK 293) cells. In some embodiments, the mammalian cells are fibrosarcoma cells (e.g., HT-1080 cells).

In some embodiments, recombinant PLGF protein is administered parenterally.

In some embodiments, the parenteral administration is selected from intravenous, intradermal, intrathecal, inhalation, transdermal (topical), intraocular, intramuscular, subcutaneous, and/or transmucosal administration.

In some embodiments, the parenteral administration is intravenous administration.

In some embodiments, the parenteral administration is subcutaneous administration.

In some embodiments, recombinant PLGF protein is administered orally.

In some embodiments, recombinant PLGF protein is administered bimonthly, monthly, triweekly, biweekly, weekly, daily, or at variable intervals.

In some embodiments, the recombinant PLGF protein is delivered to one or more target tissues selected from striated muscle (e.g., skeletal muscle, cardiac muscle). In some embodiments, the recombinant PLGF protein, is delivered to the heart. In some embodiments, the recombinant PLGF protein, is delivered to skeletal muscle. In some embodiments, the recombinant PLGF protein, is delivered to one or more skeletal muscles selected from Table 1. In some embodiments, the striated muscle (e.g., skeletal muscle) is selected from the group consisting of triceps, tibialis anterior, soleus, gastrocnemius, biceps, trapezius, deltoids, quadriceps, and diaphragm.

In some embodiments, administration of the recombinant PLGF protein results in muscle regeneration, fibrosis reduction, increased muscle strength, increased stability, increased flexibility, increased range of motion, increased stamina, reduced fatiguability, increased blood flow, improved cognition, improved pulmonary function, and/or inflammation inhibition.

In some embodiments, administration of the recombinant PLGF protein reduces the intensity, severity, or frequency, or delays the onset of at least one DMD sign or symptom. In some embodiments, administration of the recombinant PLGF protein reduces the intensity, severity, or frequency, or delays the onset of at least one DMD sign or symptom selected from the group consisting of muscle wasting, muscle weakness, muscle fragility, muscle hypertrophy, muscle pseudohypertrophy, joint contracture, skeletal deformation, cardiomyopathy, impaired swallowing, impaired bowel and bladder function, muscle ischemia, cognitive impairment, behavioral dysfunction, socialization impairment, scoliosis, and impaired respiratory function.

In some embodiments, the present invention provides a single-chain placenta growth factor (PLGF) protein comprising two fused monomers, wherein each of the two fused monomers comprises an amino acid sequence at least 70%, 80%, 85%, 90%, or 95% identical to the wild-type human PLGF protein LPAVPPQQWALSAGNGSSEVEVVP-FQEVWGRSYCRALERLVDVVSEYPSEVEHMFSPS CVSLLRCTGCCGDENLHCVPVETANVTMQLLKIRS-GDRPSYVELTFSQHVRCECRPLRE KMKPERCG-DAVPRR (SEQ ID NO: 1).

In some embodiments, a single-chain PLGF protein comprises two fused monomers wherein at least one of the two fused monomers is a wild-type human PLGF monomer (SEQ ID NO: 1).

In some embodiments, a single-chain PLGF protein comprises two fused monomers wherein at least one of the two fused monomers comprises one or more mutations at positions selected from the group consisting of Q26, W29, D71, E72, L74, and combinations thereof.

In some embodiments, a single-chain PLGF protein comprises two fused monomers wherein at least one of the two fused monomers comprises one or more mutations selected from the group consisting of Q26A, W29A, D71A, D71S, E72A, L74R, and combinations thereof.

In some embodiments, a single-chain PLGF protein comprises two fused monomers wherein the N-terminal monomer is a wild-type PLGF monomer and the C-terminal monomer comprises the one or more mutations.

In some embodiments, a single-chain PLGF protein comprises two fused monomers wherein the C-terminal monomer is a wild-type PLGF monomer and the N-terminal monomer comprises the one or more mutations.

In some embodiments, a single-chain PLGF protein comprises two fused monomers wherein the two monomers are fused via a linker.

In some embodiments, a single-chain PLGF protein comprises two fused monomers wherein the linker is a peptide comprising 3-60 amino acids.

In some embodiments, a single-chain PLGF protein comprises two fused monomers wherein a linker comprises a sequence at least 80% identical to GSTSGSGKSSEGKG (SEQ ID NO: 14).

In some embodiments, a single-chain PLGF protein is produced from mammalian cells.

In some embodiments, a single-chain PLGF protein is produced from Chinese Hamster Ovary (CHO) cells.

In some embodiments, a single-chain PLGF protein is produced from human cells.

In some embodiments, a single-chain PLGF protein is produced from human embryonic kidney cells (HEK 293).

In some embodiments, a single-chain PLGF protein is produced from human fibrosarcoma cells (e.g. HT-1080).

In some embodiments, the present invention provides a nucleic acid comprising a nucleotide sequence encoding a single-chain PLGF protein as described herein.

In some embodiments, the present invention provides a cell comprising a nucleic acid comprising a nucleotide sequence encoding a single-chain PLGF protein as described herein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only and not for limitation.

DEFINITIONS

Figure 1:
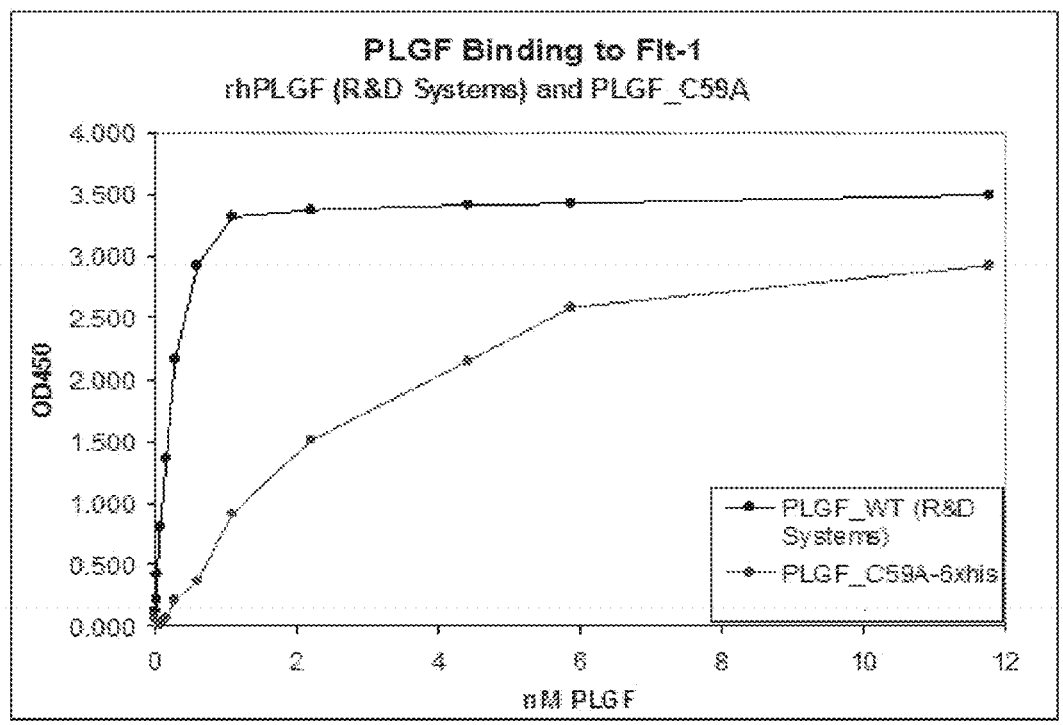
FIG. 1 shows exemplary results of recombinant human PLGF and PLGF C59A binding to Flt-1 in a plate based assay.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Bioavailability: As used herein, the term "bioavailability" generally refers to the percentage of the administered dose that reaches the blood stream of a subject.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the binding of one or more VEGF ligands, is considered to be biologically active.

Carrier or diluent: As used herein, the terms "carrier" and "diluent" refer to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Flt-1 receptor: As used herein, the term "Flt-1 receptor" includes both membrane bound and soluble Flt-1 (sFlt-1). Typically, membrane bound Flt-1 receptors include those linked to an intracellular signal transduction pathway and soluble Flt-1 receptors include those circulating and extracellular trapped Flt-1 that is not coupled to an intracellular signal transduction pathway. In some embodiments, Flt-1 receptors are also referred to as Flt-1 binding sites. In some cases, Flt-1 receptors are referred to as "decoy receptors".

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include similarities in charge, bulkiness, hydrophobicity, hydrophilicity, and the like.

Fusion Protein: As used herein, the term "fusion protein" or "chimeric protein" refers to a protein created through the joining of two or more originally separate proteins, or portions thereof. In some embodiments, a linker or spacer will be present between each protein. A non-limiting example of fusion proteins is an Fc-fusion protein (i.e., the Fc region of an immunoglobulin protein).

Half-Life: As used herein, the term "half-life" is the time required for a quantity such as protein concentration or activity to fall to half of its value as measured at the beginning of a time period.

Hypertrophy: As used herein the term "hypertrophy" refers to the increase in volume of an organ or tissue due to the enlargement of its component cells.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

PLGF or recombinant PLGF: As used herein, the term PLGF refers to any wild-type PLGF isoform (e.g., 131,152, and 203 amino-acid forms), or modified PLGF proteins (with amino acid mutations, deletions, insertions, and/or fusion proteins) that retain substantial PLGF binding and/or biological activity unless otherwise specified.

A non-limiting example of a mutation is C59A in which the cysteine at amino acid position 59 is replaced with an alanine. The C59A mutation is sometimes herein referred to as C60A (where PLGF amino acid numbering begins from a methionine at the first amino acid position). C59A and other mutations may improve the pharmacokinetic and biodistribution profiles of PLGF.

Recombinant PLGF protein: A "recombinant PLGF protein" includes dimeric and single-chain configurations of PLGF. A "single-chain PLGF protein" includes monomeric as well as single-chain dimeric configurations of PLGF. Single-chain PLGF proteins may include mutations that reduce or otherwise affect the binding of an individual PLGF monomer to Flt-1 binding sites. Non-limiting exemplary mutations in single-chain PLGF proteins, or in multi-chain dimeric PLGF include Q26A (in which the glutamine at position 26 is replaced with an alanine), W29A (in which the tryptophan at position 29 is replaced with an alanine), D71A (in which the aspartate as position 71 is replaced with an alanine), D71S (in which the aspartate at position 71 is replaced with a serine), E72A (in which the glutamate at position 72 is replaced with an alanine), L74R (in which the leucine at position 74 is replaced with an arginine).

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., DMD). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., DMD). In some embodiments a reference sample or group of reference samples are from individuals comparable to a particular individual. In some embodiments, relative risk is 0, 1, 2, 3, 4, 5, 6, 7, 8, 9, 10, or more.

Striated muscle: As used herein, the term "striated muscle" refers to multinucleated muscle tissue with regular arrangement of their intracellular contractile units, sarcomeres, leading to the appearance of striations using microscopy and under voluntary control. Typically, striated muscle can be cardiac muscle, skeletal muscle, and Branchiomeric muscles.

Smooth muscle: As used herein, the term "smooth muscle" refers to involuntarily controlled, non-striated muscle, including unitary and multi-unit muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, or more residues.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, DMD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target tissues: As used herein, the term "target tissues" refers to any tissue that is affected by a disease to be treated such as DMD. In some embodiments, target tissues include those tissues that display disease-associated pathology, symptom, or feature, including but not limited to muscle wasting, skeletal deformation, cardiomyopathy, muscle ischemia, cognitive impairment, and impaired respiratory function.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating muscular dystrophy, including Duchenne muscular dystrophy (DMD) and/or Becker muscular dystrophy, based on PLGF as a protein therapeutic. In some embodiments, the present invention provides methods of treating DMD including administering to an individual who is suffering from or susceptible to DMD an effective amount of a recombinant PLGF protein such that at least one symptom or feature of DMD is reduced in intensity, severity, or frequency, or has delayed onset.

Various aspects of the invention are described in detail in the following sections. The use of sections is not meant to limit the invention. Each section can apply to any aspect of the invention. In this application, the use of "or" means "and/or" unless stated otherwise.

Duchenne Muscular Dystrophy (DMD)

DMD is a disease characterized by progressive deterioration of muscles and loss of muscle related functions throughout the body. It is contemplated that the present invention provides methods and compositions for slowing, delaying or preventing deterioration of muscles, regenerating muscle and reversing, eliminating, delaying, preventing, or minimizing fibrosis, inflammation and other symptoms or features associated with DMD and other muscular dystrophies in various muscle tissues.

Muscle Tissues

There are two major types of muscle tissue in an animal—striated muscle and smooth muscle. As used herein, the term "striated muscle" refers to muscle tissues containing repeating sarcomeres. Striated muscle tends to be under voluntary control and attached to the skeleton. Striated muscle allows for voluntary movement of the body and includes the major muscle groups including the quadriceps, gastrocnemius, biceps, triceps, trapezius, deltoids, and many others. Striated muscle tends to be very long and, many striated muscles are able to function independently. Some striated muscle, however, is not attached to the skeleton, including those in the mouth, anus, heart, and upper portion of the esophagus.

Smooth muscle, on the other hand, has very different structure. Rather than a series of long muscles with separate skeletal attachments, smooth muscle tends to be organized into continuous sheets with mechanical linkages between smooth muscle cells. Smooth muscle is often located in the walls of hollow organs and is usually not under voluntary control. Smooth muscles lining a particular organ must bear the same load and contract concurrently. Smooth muscle functions, at least in part, to handle changes in load on hollow organs caused by movement and/or changes in posture or pressure. This dual role means that smooth muscle must not only be able to contract like striated muscle, but also that it must be able to contract tonically to maintain organ dimensions against sustained loads. Examples of smooth muscles are those lining blood vessels, bronchioles, bladder, and gastrointestinal tract such as rectum.

The strength of a muscle depends on the number and sizes of the muscle's cells and on their anatomic arrangement. Increasing the diameter of a muscle fiber either by synthesis of new myofibrils (hypertrophy) and/or the formation of more muscle cells (hyperplasia) will increase the force-generating capacity of the muscle.

Muscles may also be grouped by location or function. In some embodiments, a recombinant PLGF protein is targeted to one or more muscles of the face, one or more muscles for mastication, one or more muscles of the tongue and neck, one or more muscles of the thorax, one or more muscles of the pectoral girdle and arms, one or more muscles of the arm and shoulder, one or more ventral and dorsal forearm muscles, one or more muscles of the hand, one or more muscles of the erector spinae, one or more muscles of the pelvic girdle and legs, and/or one or more muscles of the foreleg and foot.

In some embodiments, muscles of the face include, but are not limited to, intraocular muscles such as ciliary, iris dilator, iris sphincter; muscles of the ear such as auriculares, temporoparietalis, stapedius, tensor tympani; muscles of the nose such as procerus, nasalis, dilator naris, depressor septi nasi, levator labii superioris alaeque nasi; muscles of the mouth such as levator anguli oris, depressor anguli oris, orbicularis oris, Buccinator, Zygomaticus Major and Minor, Platysma, Levator Labii Superioris, Depressor Labii Inferioris, Risorius, Mentalis, and/or Corrugator Supercilii.

In some embodiments, muscles of mastication include, but are not limited to, Masseter, Temporalis, Medial Pterygoid, Lateral Pterygoid. In some embodiments, muscles of the tongue and neck include, but are not limited to, Genioglossus, Styloglossus, Palatoglossus, Hyoglossus, Digastric, Stylohyoid, Mylohyoid, Geniohyoid, Omohyoid, Sternohyoid, Sternothyroid, Thyrohyoid, Sternocleidomastoid, Anterior Scalene, Middle Scalene, and/or Posterior Scalene.

In some embodiments, muscles of the thorax, pectoral girdle, and arms include, but are not limited to, Subclavius Pectoralis major, Pectoralis minor, Rectus abdominis, External abdominal oblique, Internal abdominal oblique, Transversus Abdominis, Diaphragm, External Intercostals, Internal Intercostals, Serratus Anterior, Trapezius, Levator Scapulae, Rhomboideus Major, Rhomboideus Minor, Latissimus dorsi, Deltoid, subscapularis, supraspinatus, infraspinatus, Teres major, Teres minor, and/or Coracobrachialis.

In some embodiments, muscles of the arm and shoulder include, but are not limited to, Biceps brachii-Long Head, Biceps brachii-Short Head, Triceps brachii-Long Head, Triceps brachii Lateral Head, Triceps brachii-Medial Head, Anconeus, Pronator teres, Supinator, and/or Brachialis.

In some embodiments, muscles of the ventral and dorsal forearm include, but are not limited to, Brachioradialis, Flexor carpi radialis, Flexor carpi ulnaris, Palmaris longus, Extensor carpi ulnaris, Extensor carpi radialis longus, Extensor carpi radialis brevis, Extensor digitorum, Extensor digiti minimi.

In some embodiments, muscles of the hand include, but are not limited to intrinsic muscles of the hand such as thenar, abductor pollicis brevis, flexor pollicis brevis, opponens pollicis, hypothenar, abductor digiti minimi, the flexor digiti minimi brevis, opponens digiti minimi, palmar interossei, dorsal interossei and/or lumbricals.

In some embodiments, muscles of the erector spinae include, but are not limited to, cervicalis, spinalis, longissimus, and/or iliocostalis.

In some embodiments, muscles of the pelvic girdle and the legs include, but are not limited to, Psoas Major, Iliacus, quadratus femoris, Adductor longus, Adductor brevis, Adductor magnus, Gracilis, Sartorius, Quadriceps femoris such as, rectus femoris, vastus lateralis, vastus medialis, vastus intermedius, Gastrocnemius, Fibularis (Peroneus) Longus, Soleus, Gluteus maximus, Gluteus medius, Gluteus minimus, Hamstrings: Biceps Femoris: Long Head, Hamstrings: Biceps Femoris: Short Head, Hamstrings: Semitendinosus, Hamstrings: Semimembranosus, Tensor fasciae latae, Pectineus, and/or Tibialis anterior.

In some embodiments, muscles of the foreleg and foot include, but are not limited to, Extensor digitorum longus, Extensor hallucis longus, peroneus brevis, plantaris, Tibialis posterior, Flexor hallucis longus, extensor digitorum brevis, extensor hallucis brevis, Abductor hallucis, flexor hallucis brevis, Abductor digiti minimi, flexor digiti minimi, opponens digiti minimi, extensor digitorum brevis, lumbricales of the foot, Quadratus plantae or flexor accessorius, flexor digitorum brevis, dorsal interossei, and/or plantar interossei.

Exemplary muscle targets are summarized in Table 1.

TABLE 1

| ORBICULARIS OCULI | | | |
|---|---|---|---|
| Intraocular: ciliary, iris dilator, iris sphincter | | | |
| Ear: auriculares, temporoparietalis, stapedius, tensor tympani | | | |
| Nose: procerus, nasalis, dilator naris, depressor septi nasi, levator labii superioris alaeque nasi | | | |
| Mouth: levator anguli oris, depressor anguli oris, orbicularis oris | | | |
| Buccinator | Zygomaticus Major and Minor | Platysma | Levator Labii Superioris |
| Depressor Labii Inferioris | Risorius | Mentalis | Corrugator Supercilii |
| Anconeus | Pronator teres | Supinator | Brachialis |
| MUSCLES OF MASTICATON | | | |
| Masseter | Temporalis | Medial Pterygoid | Lateral Pterygoid |
| MUSCLES OF THE TONGUE AND NECK | | | |
| Genioglossus | Styloglossus | Palatoglossus | Hyoglossus |
| Digastric | Stylohyoid | Mylohyoid | Geniohyoid |
| Omohyoid | Sternohyoid | Sternothyroid | Thyrohyoid |
| Sternocleidomastoid | Anterior Scalene | Middle Scalene | Posterior Scalene |
| MUSCLES OF THE THORAX, PECTORAL GIRDLE AND ARMS | | | |
| Subclavius | Pectoralis major | Pectoralis minor | Rectus abdominis |
| External abdominal oblique | Internal abdominal oblique | Transversus Abdominis | Diaphragm |
| External Intercostals | Internal Intercostals | Serratus Anterior | Trapezius |
| Levator Scapulae | Rhomboideus Major | Rhomboideus Minor | Latissimus dorsi |
| Deltoid | subscapularis | supraspinatus | infraspinatus |
| Teres major | Teres minor | Coracobrachialis | |

TABLE 1-continued

| ARM AND SHOULDER | | | |
|---|---|---|---|
| Biceps brachii-Long Head | Biceps brachii-Short Head | Triceps brachii-Long Head | Triceps brachii-Lateral Head |
| Triceps brachii-Medial Head | Anconeus | Pronator teres | Supinator |
| Brachialis | | | |

| FOREARM MUSCLES: Ventral and Dorsal | | | |
|---|---|---|---|
| Brachioradialis | Flexor carpi radialis | Flexor carpi ulnaris | Palmaris longus |
| Extensor carpi ulnaris | Extensor carpi radialis longus | Extensor carpi radialis brevis | Extensor digitorum |
| Extensor digiti minimi | erector spinae: cervicalis | erector spinae: spinalis | erector spinae: longissimus |
| erector spinae: iliocostalis | | | |

Intrinsic Muscles of the Hand: thenar, abductor pollicis brevis, flexor pollicis brevis, and the opponens pollicis
Intrinsic Muscles of the Hand: hypothenar, abductor digiti minimi, the flexor digiti minimi brevis, and the opponens digiti minimi
Intrinsic Muscles of the Hand: palmar interossei, dorsal interossei and lumbricals

| MUSCLES OF THE PELVIC GIRDLE AND THE LEGS | | | |
|---|---|---|---|
| Iliopsoas: Psoas Major | Iliopsoas: Iliacus | quadratus femoris | Adductor longus |
| Adductor brevis | Adductor magnus | Gracilis | Sartorius |
| Quadriceps femoris: rectus femoris | Quadriceps femoris: vastus lateralis | Quadriceps femoris: vastus medialis | Quadriceps femoris: vastus intermedius |
| Gastrocnemius | Fibularis (Peroneus) Longus | Soleus | Gluteus maximus |
| Gluteus medius | Gluteus minimus | Hamstrings: Biceps Femoris: Long Head | Hamstrings: Biceps Femoris: Short Head |
| Hamstrings: Semitendinosus | Hamstrings: Semimembranosus | Tensor fasciae latae | Pectineus |
| Tibialis anterior | | | |

| MUSCLES OF THE FORELEG AND FOOT | | | |
|---|---|---|---|
| Extensor digitorum longus | Extensor hallucis longus | peroneus brevis | plantaris |
| Tibialis posterior | Flexor hallucis longus | extensor digitorum brevis | extensor hallucis brevis |
| Abductor hallucis | flexor hallucis brevis | Abductor digiti minimi | flexor digiti minimi |
| opponens digiti minimi | extensor digitorum brevis | lumbricales of the foot | Quadratus plantae or flexor accessorius |
| Flexor digitorum brevis | dorsal interossei | plantar interossei | |

Muscular Dystrophy

Muscular dystrophies are a group of inherited disorders that cause degeneration of muscle, leading to weak and impaired movements. A central feature of all muscular dystrophies is that they are progressive in nature. Muscular dystrophies include, but are not limited to: Duchenne muscular dystrophy (DMD), Becker muscular dystrophy, Emery-Dreifuss muscular dystrophy, facioscapulohumeral muscular dystrophy, limb-girdle muscular dystrophies, and myotonic dystrophy Types 1 and 2, including the congenital form of Myotonic dystrophy Type 1. Symptoms may vary by type of muscular dystrophy with some or all muscles being affected. Exemplary symptoms of muscular dystrophies include delayed development of muscle motor skills, difficulty using one or more muscle groups, difficulty swallowing, speaking or eating, drooling, eyelid drooping, frequent falling, loss of strength in a muscle or group of muscles as an adult, loss in muscle size, problems walking due to weakness or altered biomechanics of the body, and/or cognitive or behavioral impairment/mental retardation.

While there are no known cures for muscular dystrophies, several supportive treatments are used which include both symptomatic and disease modifying therapies. Corticosteroids, ACE inhibitors, Angiotensin receptor Blockers, physical therapy, orthotic devices, wheelchairs, or other assistive medical devices for ADLs and pulmonary function are commonly used in muscular dystrophies. Cardiac pacemakers are used to prevent sudden death from cardiac arrythmias in Myotonic dystrophy. Anti-myotonic agents which improve the symptoms of myotonia (inability to relax) include mexilitine, and in some cases phenytoin, procainamide and quinine.

Duchenne Muscular Dystrophy

Duchenne muscular dystrophy (DMD) is a recessive X-linked form of muscular dystrophy which results in muscle degeneration and eventual death. DMD is characterized by weakness in the proximal muscles, abnormal gait, hypertrophy in the gastrocnemius (calf) muscles, and elevated creatine kinase. Many DMD patients are diagnosed around the age of 5, when symptoms/signs typically become more obvious. Affected individuals typically stop walking around age 10-13 and die in or before their mid to late 20's due to cardiorespiratory dysfunction.

The disorder DMD is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemnal membrane tearing and necrosis of muscle fibers. While both sexes can carry the mutation, females rarely exhibit severe signs of the disease.

A main symptom of DMD is muscle weakness associated with muscle wasting with the voluntary muscles being first affected typically, especially affecting the muscles of the hips, pelvic area, thighs, shoulders, and calf muscles. Muscle weakness also occurs in the arms, neck, and other areas. Calves are often enlarged. Signs and symptoms usually appear before age 6 and may appear as early as infancy. Other physical symptoms include, but are not limited to, delayed ability to walk independently, progressive difficulty in walking, stepping, or running, and eventual loss of ability to walk (usually by the age of 12); frequent falls; fatigue; difficulty with motor skills (running, hopping, jumping); increased lumbar lordosis, leading to shortening of the hip-flexor muscles; impaired functionality of Achilles tendon and hamstrings, fibrosis in connective tissue; muscle fiber deformities; pseudohypertrophy (enlarging) of tongue and calf muscles caused by replacement of muscle tissue by fat and connective tissue; higher risk of neurobehavioral disorders (e.g., ADHD), learning disorders (dyslexia), and non-progressive weaknesses in specific cognitive skills (in particular short-term verbal memory); skeletal deformities (including scoliosis in some cases).

Placenta Growth Factor

Placenta growth factor (PLGF) is a member of the cysteine-knot family of growth factors. PLGF contains intra and interchain disulfide bonds among eight spaced cysteine residues that are characteristic of cysteine-knot proteins and are involved in the formation of active dimeric proteins. Alternative splicing of the PLGF primary transcript leads to three forms of the mature human PLGF protein. The two predominant forms, PLGF-1 and PLGF-2 (also known as PLGF-131 and PLGF-152, respectively), differ only by the insertion of a highly basic 21-amino acid stretch at the carboxyl end of the protein. This additional basic region confers upon PLGF-2 the ability to bind to heparin. PLGF has been shown to bind and induce autophosphorylation of Flt-1 but not KDR/Flk-1 receptors. Without wishing to be bound by theory, it is contemplated that a recombinant PLGF binds to a Flt-1 receptor and competes with VEGF and/or other endogenous ligands to increase the amount of available VEGF or other ligands to bind to and activate other functional VEGF receptors. A Flt-1 receptor, as used herein, includes, but is not limited to, circulating, soluble Flt-1 (sFlt-1), extracellular trapped and membrane associated Flt-1 receptor.

Thus, administration of recombinant PLGF proteins promotes angiogenesis which facilitates regeneration of muscle, reduction of fibrosis and inflammation, and mitigation of symptoms and features associated with DMD and other muscular dystrophies in various muscle tissues.

Recombinant PLGF Proteins

As used herein, recombinant PLGF proteins suitable for the present invention include any wild-type and modified PLGF proteins (e.g., PLGF proteins with amino acid mutations, deletions, insertions, and/or fusion proteins) that retain substantial PLGF binding and/or biological activity. Typically, a recombinant PLGF protein is produced using recombinant technology. However, PLGF proteins (wild-type or modified) purified from natural resources or synthesized chemically can be used according to the present invention. The amino acid sequences of typical wild-type human mature PLGF proteins are shown in Table 2.

TABLE 2

| Exemplary human PLGF wild-type isoforms | |
|---|---|
| $PLGF_{131}$ (SEQ ID NO: 1) | LPAVPPQQWALSAGNGSSEVEVVPFQEVWGRSYCRAL ERLVDVVSEYPSEVEHMFSPSCVSLLRCTGCCGDENLH CVPVETANVTMQLLKIRSGDRPSYVELTFSQHVRCECR PLREKMKPERCGDAVPRR |
| $PLGF_{152}$ (SEQ ID NO: 21) | LPAVPPQQWALSAGNGSSEVEVVPFQEVWGRSYCRAL ERLVDVVSEYPSEVEHMFSPSCVSLLRCTGCCGDENLH CVPVETANVTMQLLKIRSGDRPSYVELTFSQHVRCECR PLREKMKPERRRPKGRGKRRREKQRPTDCHLCGDAVP RR |
| $PLGF_{203}$ (SEQ ID NO: 22) | LPAVPPQQWALSAGNGSSEVEVVPFQEVWGRSYCRAL ERLVDVVSEYPSEVEHMFSPSCVSLLRCTGCCGDENLH CVPVETANVTMQLLKIRSGDRPSYVELTFSQHVRCECR HSPGRQSPDMPGDFRADAPSFLPPRRSLPMLFRMEWGC ALTGSQSAVWPSSPVPEEIPRMHPGRNGKKQQRKPLRE KMKPERCGDAVPRR |

Mutant PLGF Proteins

In some embodiments, the PLGF protein contains one or more mutations that increase the biodistribution of the protein to target tissue in vivo. In some embodiments, the one or more mutations increase the Cmax in target tissue to at least more than 2 fold, 3 fold, 4 fold, 5 fold, 6 fold, 8 fold, or 10 fold compared to wild-type PLGF protein.

In some embodiments, the PLGF protein contains one or more mutations at a cysteine residue. In some embodiments, the PLGF contains substitution of an alanine for cysteine. For example, see Table 3.

TABLE 3

| Exemplary PLGF mutant with substitution of a cysteine with an alanine at position 59 | |
|---|---|
| PLGF C59A (SEQ ID NO: 2) | LPAVPPQQWALSAGNGSSEVEVVPFQEVWGRSYCRALER LVDVVSEYPSEVEHMFSPSAVSLLRCTGCCGDENLHCVPV ETANVTMQLLKIRSGDRPSYVELTFSQHVRCECRPLREKM KPERCGDAVPRR |

In some embodiments, one or more mutations are introduced into PLGF protein that alters its function. For example, one or more mutations may be made at amino acid positions that affect homo- or heterodimerization of PLGF. In some embodiments, mutations may be introduced at amino acid positions that affect the ability of PLGF to promote dimerization of cognate receptors. In some embodiments, mutations may be introduced at amino acid positions that decrease the ability of PLGF to promote dimerization of cognate receptors.

In some embodiments, mutations in an individual monomer of a single-chain PLGF protein are introduced which allow binding of PLGF to Flt-1 but reduce or prevent direct activation of Flt-1 receptors by PLGF. Without wishing to be bound by theory, it is contemplated that PLGF binding to Flt-1 receptors competes with VEGF and/or other endogenous ligands from binding thereby increasing the amount of available VEGF or other ligands to bind to and activate additional, functional VEGF receptors (e.g. VEGF 2, also known as Flk-1).

In some embodiments, one or more PLGF functional mutations are introduced into PLGF protein (including but not limited to, for example, Q26A, W29A, D71A, D71S, E72A, L74R).

TABLE 4

Exemplary PLGF mutations for single-chain PLGF protein (to retain ability to dimerize and bind to Flt-1 but not activate Flt-1) mutation shown in sequence of full-length mature PLGF monomer

| | |
|---|---|
| PLGF mutation (SEQ ID NO: 9) | LPAVPPQQWALSAGNGSSEVEVVPFQEVWGRSYCRALERL VDVVSEYPSEVEHMFSPSCVSLLRCTGCCG<u>AA</u>NLHCVPVE TANVTMQLLKIRSGDRPSYVELTFSQHVRCECRPLREKMK PERCGDAVPRR |
| PLGF mutation (SEQ ID NO: 10) | LPAVPPQQWALSAGNGSSEVEVVPFQEVWGRSYCRALERL VDVVSEYPSEVEHMFSPSCVSLLRCTGCCG<u>S</u>ANLHCVPVET ANVTMQLLKIRSGDRPSYVELTFSQHVRCECRPLREKMKP ERCGDAVPRR |
| PLGF mutation (SEQ ID NO: 11) | LPAVPPQQWALSAGNGSSEVEVVPF<u>A</u>EVWGRSYCRALERL VDVVSEYPSEVEHMFSPSCVSLLRCTGCCG<u>S</u>ANLHCVPVET ANVTMQLLKIRSGDRPSYVELTFSQHVRCECRPLREKMKP ERCGDAVPRR |
| PLGF mutation (SEQ ID NO: 12) | LPAVPPQQWALSAGNGSSEVEVVPFQEV<u>A</u>GRSYCRALERL VDVVSEYPSEVEHMFSPSCVSLLRCTGCCG<u>S</u>ANLHCVPVET ANVTMQLLKIRSGDRPSYVELTFSQHVRCECRPLREKMKP ERCGDAVPRR |
| PLGF mutation (SEQ ID NO: 13) | LPAVPPQQWALSAGNGSSEVEVVPFQEVWGRSYCRALERL VDVVSEYPSEVEHMFSPSCVSLLRCTGCCG<u>SAN</u>RHCVPVET ANVTMQLLKIRSGDRPSYVELTFSQHVRCECRPLREKMKP ERCGDAVPRR |

TABLE 5

Exemplary linker sequences for single-chain PLGF protein

| | |
|---|---|
| PLGP Linker (SEQ ID NO: 14) | GSTSGSGKSSEGKG |
| PLGF Linker (SEQ ID NO: 15) | GAPGGGGGAAAAAGGGGGAP |
| PLGF linker (SEQ ID NO: 16) | GAPGGGGGAAAAAGGGGGAPGGGGGAAAAAGG GGGAP |

TABLE 5-continued

Exemplary linker sequences for single-chain PLGF protein

| | |
|---|---|
| PLGF linker (SEQ ID NO: 17) | GAPGGGGGAAAAAGGGGGGPGGGGGAAAAAGG GGGGAPGGGGGAAAAAGGGGGAP |

In some embodiments, a recombinant PLOP protein suitable for the present invention is human PLGF (SEQ ID NO: 1). As disclosed herein, SEQ ID NO: 1 represents the amino acid sequence for the human PLGF-1 protein (PLGF$_{131}$). In some embodiments, a PLGF protein may be an alternatively spliced isoform such as PLGF$_{152}$ (SEQ ID NO: 21), or PLGF$_{203}$ (SEQ ID NO 22). In some embodiments, a suitable recombinant PLGF protein may be a homologue or an analogue of a wild-type or naturally-occurring protein. For example, a homologue or an analogue of human wild-type or naturally-occurring PLOP protein may contain one or more amino acid or domain substitutions, deletions, and/or insertions as compared to wild-type or naturally-occurring PLGF protein (e.g., SEQ ID NO: 1), while retaining substantial PLGF protein activity. Thus, in some embodiments, a recombinant PLGF protein suitable for the present invention is substantially homologous to human PLOP protein (SEQ ID NO: 1). In some embodiments, a recombinant PLGF protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 1. In some embodiments, a recombinant PLOP protein suitable far the present invention is substantially identical to human PLOP protein (SEQ ID NO: 1), In some embodiments, a recombinant PLOP protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 1.

Homologues or analogues of human PLGF proteins can be prepared according to methods for altering polypeptide sequence known to one of ordinary skill in the art such as are found in references that compile such methods. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology.

In some embodiments, a recombinant PLGF protein suitable for the present invention contains one or more amino acid deletions, insertions or replacement as compared to a wild-type human PLGF protein. For example, a suitable recombinant PLGF protein may contain amino acid substitutions at positions corresponding to 26, 29, 71, 72, and 74 of SEQ ID NO: 1.

PLGF Fusion Proteins

It is contemplated that a suitable recombinant PLGF protein can be in a fusion protein configuration. For example, a recombinant PLGF protein suitable for the present invention may be a fusion protein between a PLGF domain and another domain or moiety that typically can facilitate a therapeutic effect of PLGF by, for example, enhancing or increasing stability, potency and/or delivery of PLGF protein, or reducing or eliminating immunogenicity or toxicity. Such suitable domains or moieties for a PLGF fusion protein include but are not limited to Fc domain, albumin fusion proteins, and XTEN domains.

In some embodiments, a suitable recombinant PLGF protein contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. Particularly suitable Fc domains include those derived from human or humanized antibodies.

In some embodiments, a suitable Fc domain comprises an amino acid sequence shown below

```
                                           (SEQ ID NO: 18)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK.
```

In some embodiments, a suitable Fc domain comprises an amino acid sequence shown below

```
                                           (SEQ ID NO: 19)
EPKSXDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK,
wherein X is any amino acid other than cysteine.
```

In some embodiments, a suitable Fc domain comprises an amino acid sequence shown below

```
                                           (SEQ ID NO: 20)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTIPPVLDSDGSFFLYSKLTVDKSRWQQG

NVFSCSVMHEALHNHYTQKSLSLSPGK.
```

In some embodiments, a suitable Fc domain comprises an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO: 18.

In some embodiments, a suitable Fc domain comprises an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO: 19.

In some embodiments, a suitable Fc domain comprises an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO: 20.

It is contemplated that improved binding between Fc domain and the FcRn receptor results in prolonged serum half-life. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433, and/or Asn 434 of human IgG1.

Typically, a suitable recombinant PLGF protein, in particular a mutated PLGF protein or PLGF protein fused to an Fc protein, has an in vivo half-life of or greater than 1 hour, 1.5 hours, 2 hours, 2.5 hours, 3 hours, 3.5 hours, 4 hours, 5 hours, 6 hours, 7 hours, 8 hours, 9 hours, 10 hours, 11 hours, 12 hours, 24 hours, 1.5 days, 2 days, 2.5 days, 3 days, 3.5 days, 4 days, 4.5 days, or 5 days.

Linker or Spacer

A PLGF domain may be directly or indirectly linked to an Fc domain. In some embodiments, a suitable recombinant PLGF protein contains a linker or spacer that joins a PLGF domain and an Fc domain. An amino acid linker or spacer is generally designed to be flexible or to interpose a structure, such as an alpha-helix, between the two protein moieties. A linker or spacer can be relatively short, or can be longer. Typically, a linker or spacer contains for example 3-60 (e.g., 5-55, 10-50, 10-45, 10-40, 10-35, 10-30, 10-25, 10-20) amino acids in length. Typically, a longer linker may decrease steric hindrance. In some embodiments, a linker will comprise a mixture of glycine and serine residues. In some embodiments, the linker may additionally comprise threonine, proline and alanine residues.

As non-limiting examples, linkers or spacers suitable for the present invention include but are not limited to:

GSTSGSGKSSEGKG; (SEQ ID NO: 14)

GAPGGGGAAAAAGGGGGAP; (GAG linker, SEQ ID NO: 15)

GAPGGGGAAAAAGGGGGAPGGGGGAAAAAGGGGGAP; (GAG2 linker, SEQ ID NO: 16)

GAPGGGGAAAAAGGGGGAPGGGGGAAAAAGGGGGAPGGGGGAAAAAGGGGGAP; (GAG3 linker, SEQ ID NO: 17)

and

Suitable linkers or spacers also include those having an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to the above exemplary linkers (SEQ ID NOs: 14-17).

Exemplary PLGF Fusion Proteins

In particular embodiments, a suitable recombinant PLGF fusion protein includes a PLGF polypeptide, an Fc domain, and a linker that associates the PLGF polypeptide with the Fc domain, wherein the PLGF polypeptide comprises an amino acid sequence at least 50%, 55%, 60%, 65%, 70%, 75%, 80%, 85%, 90%, 91%, 92%, 93%, 94%, 95%, 96%, 97%, 98%, 99% or 100% identical to the wild-type human PLGF protein (SEQ ID NO: 1) or a variant PLGF protein (SEQ ID NO: 2); and further wherein the recombinant PLGF fusion protein has an in vivo half-life in circulation ranging from about 0.5-6 days (e.g., about 0.5-5.5 days, about 0.5-5 days, about 1-5 days, about 1.5-5 days, about 1.5-4.5 days, about 1.5-4.0 days, about 1.5-3.5 days, about 1.5-3 days, about 1.5-2.5 days, about 2-6 days, about 2-5.5 days, about 2-5 days, about 2-4.5 days, about 2-4 days, about 2-3.5 days, about 2-3 days).

It is contemplated that a PLGF-Fc fusion protein may be provided in various configurations including homodimeric or monomeric configurations. For example, a suitable homodimeric configuration may be designed to have the C-terminal end of fusion partner (e.g., a PLGF polypeptide plus linker) attached to the N-terminal end of both Fc polypeptide strands. A suitable monomeric configuration may be designed to have the C-terminal end of fusion partner (e.g., a PLGF polypeptide plus linker) fused to one Fc dimer. A monomeric configuration may decrease steric hindrance.

Production of PLGF Proteins

A recombinant PLGF protein suitable for the present invention may be produced by any available means. For example, a recombinant PLGF protein may be recombinantly produced by utilizing a host cell system engineered to express a recombinant PLGF protein-encoding nucleic acid. Alternatively or additionally, a recombinant PLGF protein may be produced by activating endogenous genes. Alternatively or additionally, a recombinant PLGF protein may be partially or fully prepared by chemical synthesis.

Where proteins are recombinantly produced, any expression system can be used. To give but a few examples, known expression systems include, for example, egg, baculovirus, plant, yeast, or mammalian cells.

In some embodiments, recombinant PLGF proteins suitable for the present invention are produced in mammalian cells. Non-limiting examples of mammalian cells that may be used in accordance with the present invention include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, the present invention provides recombinant PLGF proteins produced from human cells. In some embodiments, the present invention provides recombinant PLGF proteins produced from CHO cells. In some embodiments, the present invention provides recombinant PLGF proteins produced from fibrosarcoma cells. In some embodiments, the present invention provides recombinant PLGF proteins produced from human embryonic kidney (HEK 293) cells.

Typically, cells that are engineered to express a recombinant PLGF protein may comprise a transgene that encodes a recombinant PLGF protein described herein. It should be appreciated that the nucleic acids encoding recombinant PLGF protein may contain regulatory sequences, gene control sequences, promoters, non-coding sequences and/or other appropriate sequences for expressing the recombinant PLGF protein. Typically, the coding region is operably linked with one or more of these nucleic acid components.

The coding region of a transgene may include one or more silent mutations to optimize codon usage for a particular cell type. For example, the codons of a PLGF transgene may be optimized for expression in a vertebrate cell. In some embodiments, the codons of a PLGF transgene may be optimized for expression in a mammalian cell. In some embodiments, the codons of a PLGF transgene may be optimized for expression in a human cell. In some embodiments, the codons of a PLGF transgene may be optimized for expression in CHO cells.

Production of Single-Chain PLGF

PLGF is expressed in mammalian cells, or expressed in bacteria and then refolded. Remove signal peptide sequence at N terminus. Production of a single-chain polypeptide is discussed in Boesen et al. (2002) *J. Biol. Chem.* 277(43): 40335-41. A modified method of Boesen for production of single chain PLGF and PLGF mutants is described in Example 1.

Pharmaceutical Composition and Administration

The present invention further provides a pharmaceutical composition containing a recombinant PLGF protein described herein and a physiologically acceptable carrier or excipient.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

A recombinant PLGF protein described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Routes of Administration

A recombinant PLGF protein described herein (or a composition or medicament containing a recombinant PLGF protein described herein) is administered by any appropriate route. In some embodiments, a recombinant PLGF protein or a pharmaceutical composition containing the same is administered parenterally. Parenteral administration may be intravenous, intradermal, inhalation, intrathecal, transdermal (topical), intraocular, intramuscular, subcutaneous, intramuscular, and/or transmucosal administration. In some embodiments, a recombinant PLGF protein or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, a recombinant PLGF protein or a pharmaceutical composition containing the same is administered intravenously. In some embodiments, a recombinant PLGF protein or a pharmaceutical composition containing the same is administered orally. More than one route can be used concurrently, if desired.

In some embodiments, administration results only in a localized effect in an individual, while in other embodiments, administration results in effects throughout multiple portions of an individual, for example, systemic effects. Typically, administration results in delivery of a recombinant PLGF protein to one or more target tissues including but not limited to kidney, liver, lung, spleen, heart, brain, spinal cord, intestinal tract, eye, striated muscle, and smooth muscle.

Dosage Forms and Dosing Regimen

In some embodiments, a composition is administered in a therapeutically effective amount and/or according to a dosing regimen that is correlated with a particular desired outcome (e.g., with treating or reducing risk for a muscular dystrophy, such as DMD).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, a recombinant PLGF protein is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a muscular dystrophy, such as DMD.

In some embodiments, a formulation comprising a recombinant PLGF protein described herein administered as a single dose. In some embodiments, a formulation comprising a recombinant PLGF protein described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a recombinant PLGF protein described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a recombinant PLGF protein described herein is administered at regular intervals indefinitely. In some embodiments, a formulation comprising a recombinant PLGF protein described herein is administered at regular intervals for a defined period.

In some embodiments, administration of a recombinant PLGF protein reduces the intensity, severity, or frequency, or delays the onset of at least one DMD sign or symptom. In some embodiments administration of a recombinant PLGF protein reduces the intensity, severity, or frequency, or delays the onset of at least one DMD symptom selected from the group consisting of muscle wasting, skeletal deformation, cardiomyopathy, muscle ischemia, cognitive impairment, and impaired respiratory function.

In some embodiments, administration of a recombinant PLGF protein improves clinical outcome as measured by a 6 minute walk test, quantitative muscle strength test, timed motor performance test, Brooke and Vignos limb function scales, pulmonary function test (forced vital capacity, forced expiratory volume in 1 second, peak expiratory flow rate, maximal inspiratory and expiratory pressures), health-related quality of life, knee and elbow flexors, elbow extensors, shoulder abduction, grip strength, time to rise from supine position, North Start Ambulatory Assessment, timed 10 meter walk/run, Egen-Klassification scale, Gowers score, Hammersmith motor ability, hand held myometry, range of motion, goniometry, hypercapnia, Nayley Scales of Infant and Toddler Development, and/or a caregiver burden scale.

Combination Therapy

In some embodiments, a recombinant PLGF protein is administered in combination with one or more known therapeutic agents (e.g., corticosteroids) currently used for treatment of a muscular dystrophy. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXAMPLES

Example 1. Production of PLGF Single-Chain Mutants

A sequence spanning the 3'-5' nucleotides of the first PLGF gene (starting with the recognition sequence for the restriction endonuclease NgoMIV and excluding the stop codon), a 42 nucleotide linker (encoding SEQ ID NO: 14) and the second PLGF gene and a PmeI restriction site were synthesized in vitro. The amino acid sequence was back translated into a nucleotide sequence using the codon usage for highly expressed human genes. Further adaptations of the codon usage were made in order to prevent high GC content as well as direct or inverted sequence repeats within the 3' PLGF sequence as well as with the 5' PLGF sequence. The 5' PLGF gene was cut with NheI and NgoMIV and inserted together with the linker-3' PLGF sequence (NgoMIV, PmeI) into the expression vector pX671. Mutations in the 3' PLGF coding sequence were introduced using the QUICKCHANGE mutagenesis kit from AGILENT and resulting fragment was inserted into the expression vector as described for the wildtype sequence. The coding sequence for a Tev protease cleavage site as well as a 6 Histidine tag was added to the 3'-end of all single chain PLGF genes by PCR.

Single chain PLGF mutants scQ26A/D71S/E72A Tev-His and scQD71S/E72A Tev-His were expressed in human fibrosarcoma cells. Human fibrosarcoma cells were stably transfected with an expression plasmid for scQ26A/D71S/E72A or scQD71S/E72A Tev-His. A single stable clone was established and media production was initiated in shaker flasks.

Single chain PLGF mutants scQ26A/D71S/E72A and scQD71S/E72A Tev-His expressing cells were seeded at a cell density of $1 \times 10^6$ cells/ml and then conditioned media (CM) collection was initiated. CM was harvest daily from shaker flasks and cells were refed with fresh media. Production was carried out at 37° C.

Clarified CM from cell lines expressing scQ26A/D71S/E72A Tev-His and scQD71S/E72A Tev-His was brought to room temperature and purified over a Nickel column with a gradient elution. The fractions containing the purified target proteins were pooled, buffer exchanged into storage buffer and concentrated to the final storage condition.

Example 2. Production of PLGF C59A Mutant

The 236 C-terminal nucleotides of the PLGF gene excluding the stop codon were amplified by PCR. The forward amplification primer spanned the Pci I restriction site at nucleotide 212 of the coding sequence and contained a TG to GC mutation at nucleotide 229 and 230 of the coding sequence (introducing the C59 to A mutation in the PLGF C59A protein). The reverse amplification primer added a Tev protease cleavage site and a 6 Histidine tag as well as a PmeI restriction site to the 3' end of the PLGF coding sequence. The PCR fragment was inserted together with the 5' end of the wt PLGF cut with NheI and PciI into the NheI and PmeI restrictions site of the pX671 expression vector.

PLGF C59A was expressed in human fibrosarcoma cells. Fibrosarcoma cells were stably transfected with an expression plasmid for PLGF C59A. A single stable clone was established and media production was initiated using a GE Wave Bioreactor. PLGF C59A expressing cells were grown to a cell density of $1 \times 10^6$ cells/ml and then conditioned media (CM) collection was initiated. CM production was carried out in perfusion mode at 37° C.

Clarified CM was brought to room temperature and purified over a Nickel column with a gradient elution. The fractions containing purified protein were pooled, buffer exchanged into storage buffer and concentrated to the final storage condition.

Example 3. Wild-Type and Mutant PLGF Binding Assays

Plate Based Assays

A plate based assay was performed to examine the binding of mutant PLGF protein to Flt-1. Briefly, plates were coated with a mouse monoclonal anti-Flt-1 antibody for capture. After washing and blocking steps, 250 ng/ml of Flt-1 receptor was incubated with WT PLGF (0-400,000 pg/ml) or PLGF C59A (0-40,000 pg/ml) in the plate. After further washing steps, bound WT or mutant PLGF were detected using a biotinylated goat anti-PLGF antibody and streptavidin-HRP immunodetection system. PLGF C59A appeared to bind Flt-1 with lower affinity than WT PLGF. (FIG. 1).

Figure 6:
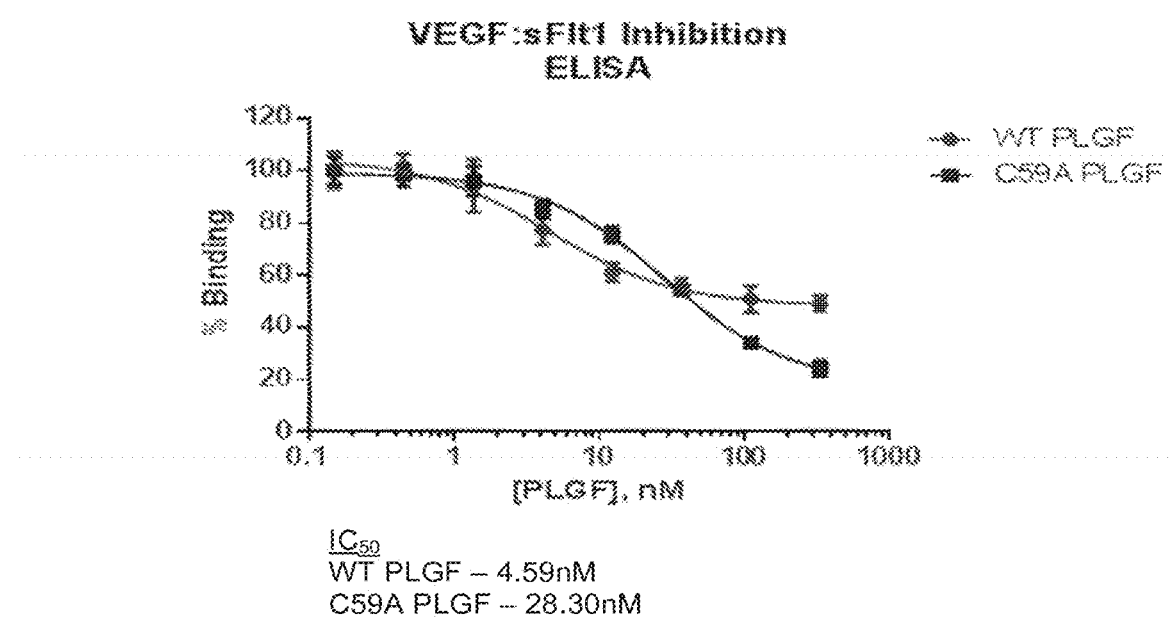
FIG. 6 shows exemplary results of WT PLGF and PLGF C59A inhibition of binding of VEGF to sFlt-1 by ELISA.

Inhibition of binding of VEGF to sFlt-1 by WT PLGF and PLGFC59A was also assessed by ELISA. The addition of recombinant human sFlt-1 inhibited binding of recombinant VEGF to recombinant human sFlt-1 chimera (FIG. 6). Binding of human sFlt-1 Fc to immobilized human VEGF was quantified by immunodetection with HRP conjugated anti-human IgG Fc. Data were normalized to binding sFlt-1 Fc to VEGF in the absence of PLGF.

Surface Plasmon Resonance Assay

Binding characteristics of PLGF C59A and WT PLGF with sFlt-1 was investigated using the label-free binding technology, surface plasmon resonance, on BIACORE model T200. Direct coupling (amine or ligand thiol immobilization) or Capture (using goat anti-hIgG Fc (Cat #109-005-098, JACKSON IMMUNORESEARCH LAB) approaches was adopted based on protein nature and experimental design. In most cases, multi-cycle kinetic approach was used for the binding kinetic study. The single cycle kinetic approach was only used in slow dissociation system.

All binding assays were conducted at 25° C. in HBS-EP+ buffer (GE) at a flow rate 30 µL/min. Protein analyte concentrations were varied based on $K_D$ values. In general, at least 5 different concentrations, from above $K_D$ to below $K_D$, were applied. The resulting sensorgrams were fitted by BIA-EVALUATION software (Version 1.0) using a 1:1 binding model. The association rate (Ka), dissociation rate (Kd) and equilibrium dissociation constant $K_D$ were reported.

In the single cycle kinetic approach, PLGF C59A at 50 µg/ml in 10 mM acetate buffer pH 5.0 was immobilized via ligand thiol coupling to ~200 RU. sFlt-1-Fc dimer was serially diluted in HBS-EP+ running buffer from 30 to 1.875 nM. The sFlt-1-Fc dimer was injected from low to high concentration sequentially, without dissociation phase and regeneration step. The association step was 180 seconds per injection at 30 µL/min. At the end of the last injection, one single dissociation step was performed at 30 µL/min, for one hour to collect sufficient dissociation data.

In the capture approach, goat anti-hIgG Fc polyclonal antibody (30 µg/mL in 10 mM acetate buffer, pH 5.0) was immobilized onto a CM5 chip by amine coupling. The immobilization level or surface density of anti-hIgG Fc antibody was controlled between 6000 to 8000 RU. For the kinetic study, sFlt-1-Fc was captured on the surface that was immobilized with the anti-hIgG Fc antibody, before each injection of PLGF variants. The capture level of sFlt-1-Fc (10 µg/mL) was controlled by varying contact time, 10 to 30 seconds, at flow rate 10 µL/min. PLGF variants, as analytes, were serially diluted in HBS-EP+ buffer from 50 to 0.03 nM, and injected to the surface that captured sFlt-1-Fc. The association time for each PLGF variants injection was 300 seconds at 30 µL/min and dissociation time was 600 seconds at the same flow rate. After each round of PLGF variants' injection, a regeneration of 0.1 mM H3PO4 pH1.8 at 60 µl/min for 90 seconds was performed. The regeneration step effectively removes the complex of sFlt-1-Fc and PLGF variants from the surface that was immobilized with anti-hIgG Fc antibody. A stabilization step was applied for 90 seconds after regeneration.

Example 4. Comparison of PLGF C59A and WT PLGF with Human and Mouse sFlt-1 by Surface Plasmon Resonance Human sFlt-1 (hsFlt-1)

Two BIACORE experiment formats, single cycle kinetics and anti-Fc capture approach, were used to study binding characteristic of PLGF variants with hsFlt-1.

Due to the nonspecific binding of hsFlt-1 on the reference cells and the poor regeneration conditions for PLGF C59A, a single cycle kinetic method were adopted by immobilizing PLGF C59A vial thiol coupling, and injecting hsFlt-1 as analyte. In the single cycle kinetic approach, PLGF C59A was immobilized onto CM4 chips through free cysteine residuals, C69 and C125, in PLGF C59A. Concentration of the Flt1-Fc dimer injected was varied from 0.37 to 30 nM. The binding characteristics, association rate constant (Ka), dissociation rate constant (Kd) and equilibrium dissociation constant ($K_D$), are summarized in Table 6.

Capture approach was deployed by capturing hsFlt-1-Fc fusion protein via anti-Fc antibody (goat anti-hIgG Fc, Jackson Immunoresearch lab Cat #109-005-098), and injecting PLGF variants after each capture. Two capture levels, 250 and 500 RU of hsFlt-1-Fc were used for study of human WT PLGF, PLGF C59A R1 and PLGF C59A RC4 (pool 1, a higher purity population). The consistency of binding kinetic data in two different capture levels indicates that binding kinetic data determined is independent of surface density.

In summary, the equilibrium dissociation constants determined by the single cycle kinetic method and capture method are comparable. The affinity of PLGF C59A with hsFlt-1-Fc dimer was significantly less than WT PLGF with hsFlt-1-Fc dimer, about 20-30 fold.

Also, higher affinity was observed for PLGF C59A R1 which contains significant amount of dimers (24.4%) along with monomer (55.3%), than PLGF C59A RC4 which contains 97% monomer indicating affinity of monomeric PLGF C59A is most likely lower than PLGF C59A dimer.

Mouse sFlt-1 (msFlt-1)

The binding characteristics of PLGF variants, PLGF C59A, human WT PLGF and mouse WT PLGF, with msFlt-1 were studied in the mouse model. The same capture approach for hsFlt-1 was used for the msFlt-1. The binding data are summarized in Table 6.

In summary, the affinity of PLGF C59A with msFlt-1 is ~90-fold weaker than human WT PLGF, and is ~250-fold weaker than mouse WT PLGF. The affinities of human and mouse WT PLGF with msFlt-1 are comparable, and they are also comparable to the affinities of human WT PLGF with hsFlt-1.

Example 5. In-Solution Isothermal Titration Calorimetry (ITC) Binding Assay

Figure 2:
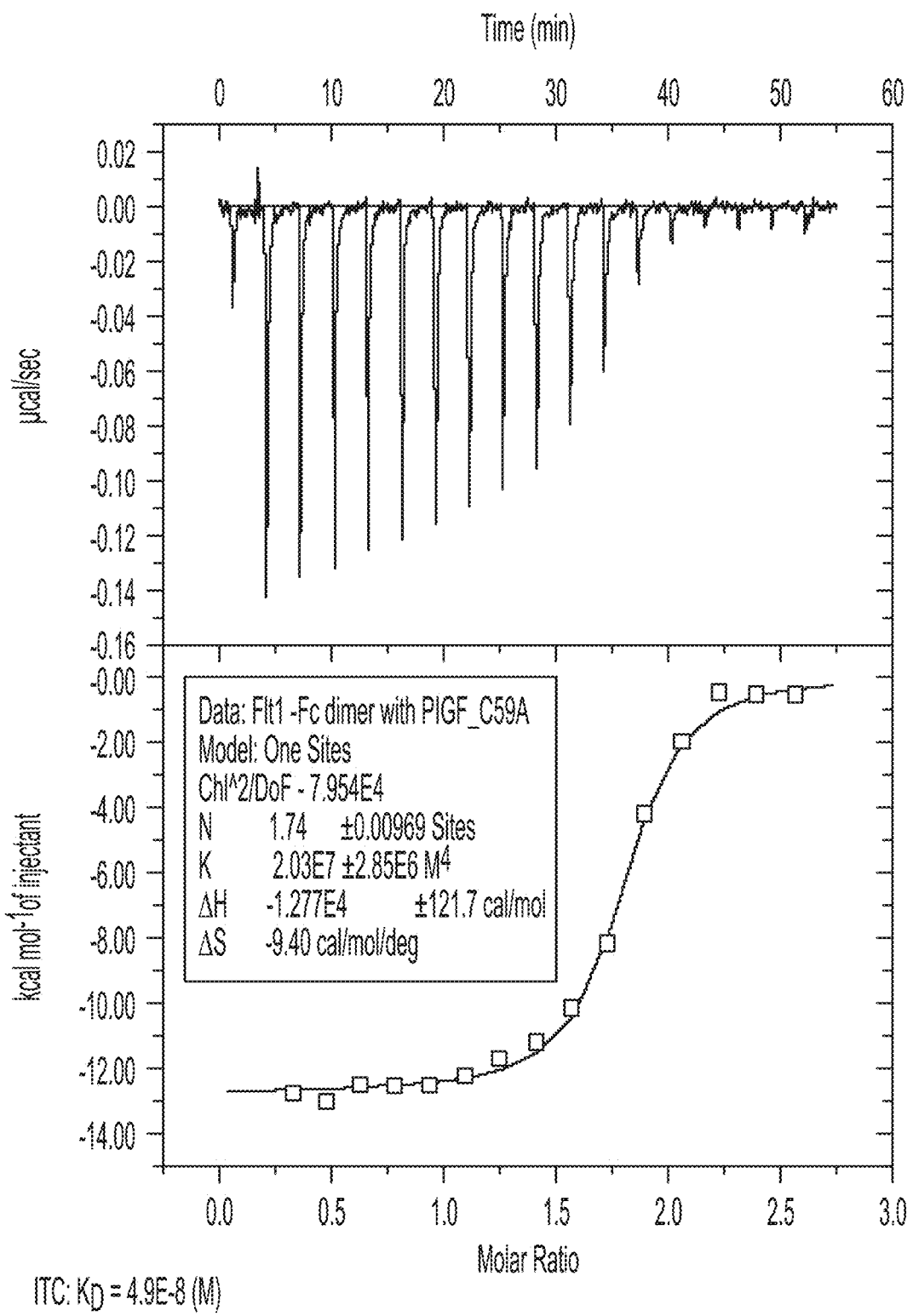
FIG. 2 shows exemplary results of in-solution binding affinity of PLGF C59A to human sFlt-1 in an isothermal titration calorimetry (ITC) assay.
Figure 3:
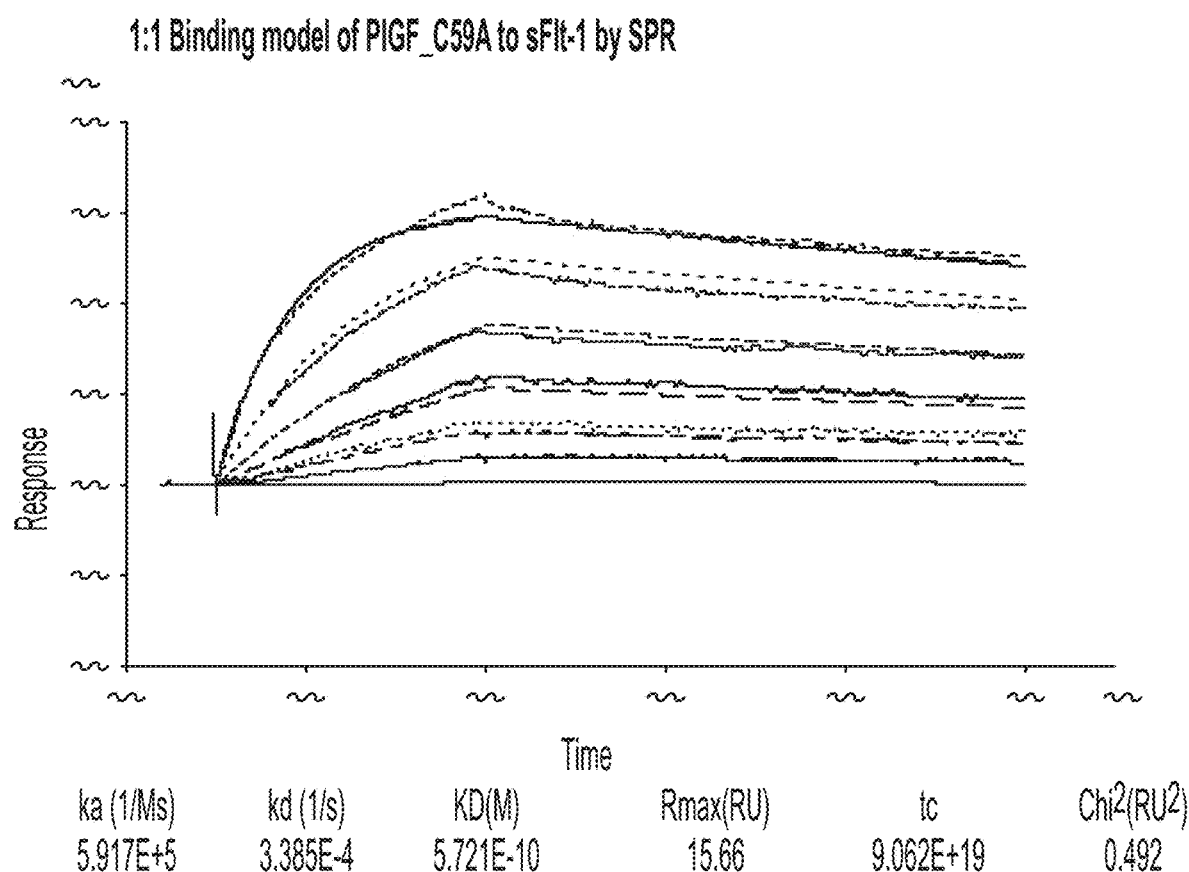
FIG. 3 shows exemplary results of binding of PLGF C59A to sFlt-1 in a surface plasmon resonance assay.

PLGF C59A and human sFlt-1-Fc (Cat #321-FL/CF, R&D System) were extensively dialyzed against PBS pH 7.4 buffer overnight. After dialysis, the proteins were concentrated using VIVISPIN 500 (10 kDa Cutoff, Cat # vs0601). The ratio of PLGF C59A in syringe to sFlt-1-Fc in the cell was about 10:1, with PLGF C59A concentration to be 77 μM, and the concentration of sFlt1-Fc to be 5.3 μM. Titrations were carried out using 2.0-μL injections for total 18 injections. An initial 2-μl injection was carried out but the data not included in the final data analysis. All titrations were done at 25° C. The binding isotherm was fitted with nonlinear regression on ORIGIN (GE MICROCAL, INC). The stoichiometry (N) of the binding interaction, the equilibrium association constant ($K_A$) and enthalpy (ΔH) of the complex formation were calculated from the titration data. C59A PLGF was determined to bind to an Flt-1-Fc dimer with a $K_D$ of about 49 nM in the isothermal titration calorimetry (ITC) assay (FIG. 2).

Example 6. Crosslinking of PLGF and sFlt-1 Binding Complexes

Crosslinking techniques were utilized to determine stoichiometry of WT PLGF and PLGF C59A interacting with hsFlt-1. A commercial sFlt-1 that doesn't contain Fc fusion was used for the crosslinking study.

PLGF and sFlt-1 (Human sFlt-1:Abcam, Cat #54346) were incubated on ice for 2 hrs in 100 μL crosslinking buffer. After the incubation, the crosslinking reagent, Disuccinimidyl suberate (DSS), was added, 1 μL of 25 mM stock DSS (in DMSO) to a final concentration of 250 μM. After brief vortexing, the mixture was incubated on ice for additional 15 min.

The mixture containing the crosslinked complexes of PLGF and sFLT-1 were precipitated by standard TCA method (100% (w/v) TCA). The pellet was spun down at maximum speed on microcentrifugation for 10 minutes. The supernatant was discarded, and the pellets were then washed twice with 200 μl acetone. After removal of the acetone wash solution, the pellet was dried by heating at 40° C. in a heat block with caps open.

To analyze the crosslinked complexes using Western blot, the pellets were solubilized with 30 μL of 1×LDS buffer containing 10 mM DTT. After heating the dissolved pellets to 37° C. for 15 min, 10 μL of the sample was loaded onto 8 to 16% Tris-glycince SDS-PAGE gel. The gels were transferred to PVDF membranes by standard method for anti-PLGF or anti-Flt-1 Western blot analysis.

WT PLGF forms dimers in its native state, and the binding models of WT PLGF with hsFlt-1 were established. A PLGF C59A monomer binding with Flt-1 receptor monomer is also found. The binding complexes, WT PLGF-hsFlt-1 and PLGF C59A-hsFlt-1, were crosslinked by DSS through amine groups on the surface of PLGF or hsFlt-1 molecules. After separating on SDS-PAGE, PLGF-containing or Flt-1 containing binding complexes were detected on Western blot by anti-PLGF or anti-Flt-1 antibodies.

The following samples were applied to the Western blot analysis
- PLGF-hsFLT-1 binding complexes with/without crosslinking reagent
- hsFlt-1 with/without crosslinking reagent treatment
- PLGF C59A and WT PLGF, with/without crosslinking reagent treatment.

Figure 4:
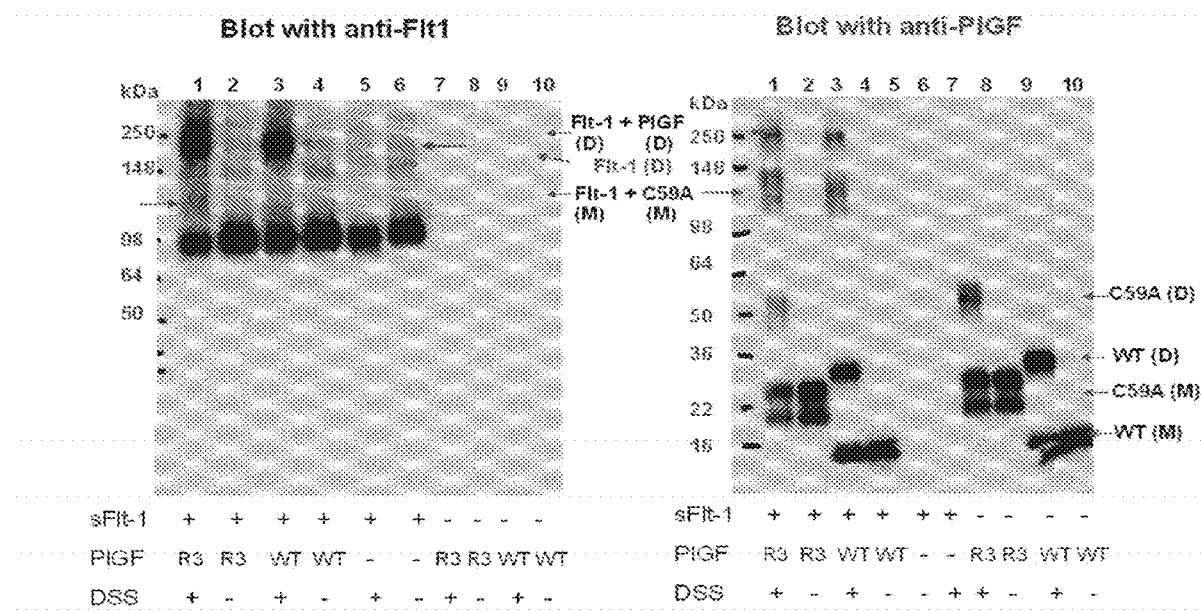
FIG. 4 shows exemplary results of WT PLGF and PLGF C59A binding to human sFlt-1 by protein crosslinking.

The following species or binding complexes were identified on the Western blot (See FIG. 4).
- A 250 kDa band could be detected in both anti PLGF and anti Flt-1 blots, on lane 1 and lane 3, indicating the dimer-dimer formation of PLGF C59A with hsFlt-1, and WT PLGF with hsFlt-1.
- Anti Flt-1 Western blot showed hsFlt-1 monomer only. No hsFlt-1 dimer formed in the absence of PLGF (lane 5 on anti Flt-1 blot), which indicates that the dimerization of Flt-1 receptor is triggered by the PLGF binding to the receptor.
- Anti-PLGF Western blot showed WT PLGF and PLGF C59A monomers. Anti-PLGF Western blot also showed dimmers of the WT PLGF and dimmers of PLGF C59A, respectively in the absence of hsFlt-1 receptor.
- On the anti-PLGF Western blot, on lane 1 and 3, the bands between 98 and 148 kDa were only formed in the presence of hsFlt-1 receptor, indicating the monomer-monomer complexes of PLGF variants and hsFlt-1. Due to the lack of clear corresponding bands on the anti-Flt-1 blot, monomer-monomer complexes could not be confirmed.

In summary, the crosslinking experiments confirmed the well-established dimer-dimer binding model of WT PLGF with hsFlt-1, and the dimer formation of WT PLGF in its native state. PLGF C59A has similar behavior as WT PLGF in terms of forming intermolecular dimers, and forming dimer-dimer complexes with hsFlt-1, albeit to a lesser degree than WT PLGF.

TABLE 6

SPR Affinities of PLGF binding to mouse or human sFlt-1 (1:1 Binding Model)

| Samples | Ligands | Ka (1/Ms) | Kd (1/s) | KD (M) | KD (M) Average |
|---|---|---|---|---|---|
| Human WT-PLGF | Mouse sFlt-1 | 2.734E+6 | 2.434E−4 | 8.901E−11 | 5.646E−11 |
|  |  | 6.359E+6 | 1.520E−4 | 2.391E−11 |  |
| Human PLGF_C59A (R3) |  | 8.772E+4 | 6.330E−4 | 7.217E−9 | 5.171E−9 |
|  |  | 1.588E+5 | 4.961E−4 | 3.124E−9 |  |
| Mouse WT-PLGF |  | 4.494E+6 | 1.351E−4 | 3.006E−11 | 2.050E−11 |
|  |  | 8.859E+6 | 9.686E−5 | 1.093E−11 |  |
| Human WT-PLGF | Human sFlt-1 | 2.329E+6 | 6.030E−5 | 2.589E−11 | 4.048E−11 |
|  |  | 1.608E+6 | 8.859E−5 | 5.508E−11 |  |
| Human PLGF_C59A (RC4.96% Monomer) |  | 2.310E+5 | 3.719E−4 | 1.610E−9 | 1.248E−9 |
|  |  | 2.636E+5 | 2.337E−4 | 8.864E−10 |  |

Example 7. Wild-Type and Mutant PLGF Dimerization

Wild Type-PLGF forms homodimers through two intermolecular disulfide bonds via the two cysteine residues, C59 and C68. To generate monomer, one of the cysteine residue, C59 was mutated to Alanine, hence the PLGF C59A mutant.

MALS was used to study the association state of the PLGF C59A after separating on SE-HPLC column. The percentage of the monomer and aggregate of PLGF C59A was also determined on SE-HPLC chromatography.

The SEC-MALS analysis estimated that PLGF C59A (R1) molar mass to be 18,100 g/mol and 39,200 g/mol. The theoretical monomer mass is 16,395 g/mol. The difference between experimental and the theoretical molar mass is most likely due to glycosylation of PLGF C59A, which was confirmed by deglycosylation of PLGF C59A and examined on SDS-PAGE gel (RDR 75-FLT-12-1839). The high molecular weight species at a molar mass of 39,200 g/mol are likely PLGF C59A dimers.

SE-HPLC method was used to determine percentage of monomer and oligomer in various lots of PLGF C59A samples, and the results are summarized in Table 7. The following samples were analyzed on SE-HPLC.

PLGF C59A R1: Nickel affinity column purified
PLGF C59A RC4: Nickel column followed with Size-exclusion purified
PLGF C59A R3: Nickel purified PLGF C59A formulated in 1 mM DTT
PLGF C59A R4: Nickel purified PLGF C59A formulated in 1 mM DTT SE-HPLC of PLGF C59A indicated that nickel affinity column combined with SEC column removed significant amount of aggregates, and results in content of monomer up to 96.7%. But, similar monomer content could be achieved by supplementing 1 mM DTT in formulation buffer, after one step purification on Nickel column.

TABLE 7

Purity of PLGF C59A determined by SE-HPLC

| Sample | % Monomer | % Dimer | % High-order aggregates |
|---|---|---|---|
| R1 | 55.3 | 24.4 | 20.3 |
| RC4 | 96.7 | 3.1 | 0.2 |
| R3 | 97.1 | 2.8 | 0.1 |
| R4 | 97.3 | 2.4 | 0.3 |

Example 8. Single Chain Mutant PLGF Binding to Flt-1

Figure 5:
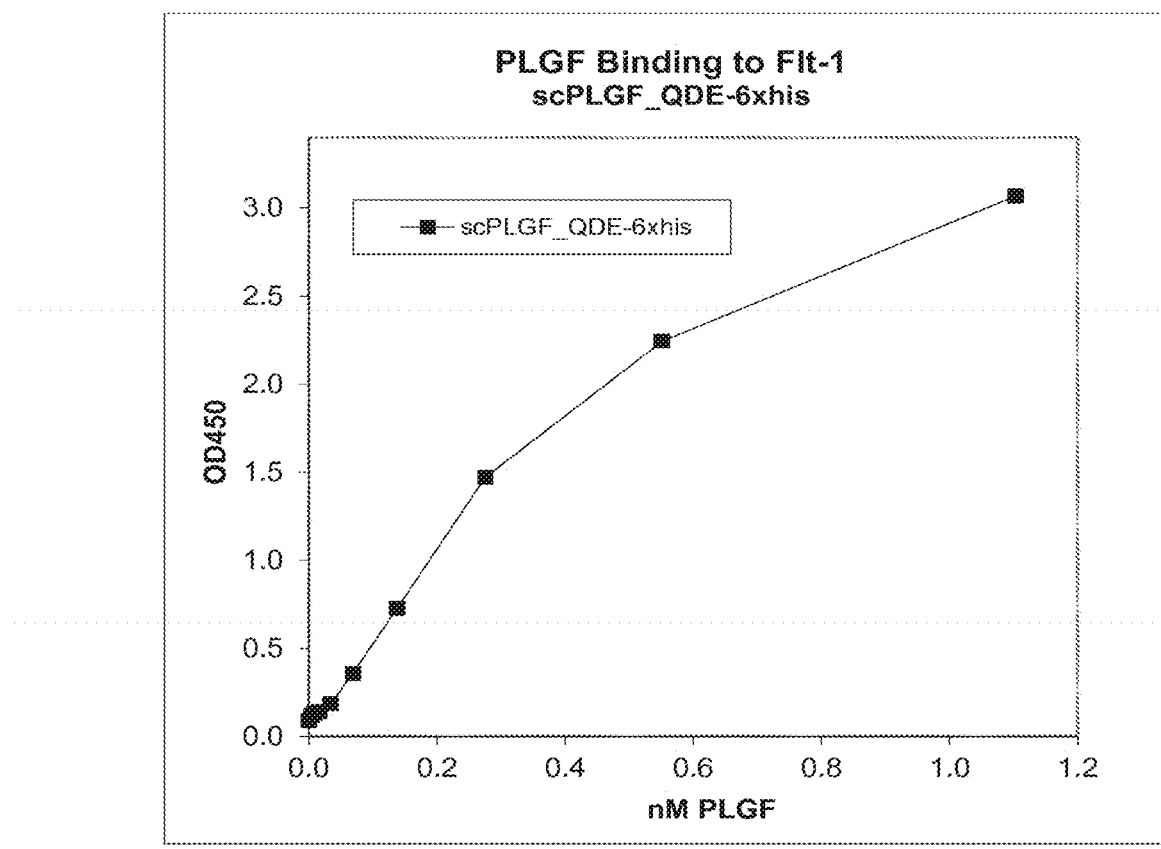
FIG. 5 shows exemplary results of a single chain PLGF mutant (containing mutations Q26A, D71S, and E72A) binding to Flt-1 by a plate based assay.

A plate based assay was performed similar to as described in Example 3 to examine the binding of mutant single chain PLGF proteins to Flt-1. A single chain PLGF protein containing the mutations Q26A, D71S, and E72A (as shown in SEQ ID NO: 11) was demonstrated to bind to Flt-1 in a concentration dependent manner (FIG. 5).

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method of inducing angiogenesis in an individual suffering from Duchenne Muscular Dystrophy (DMD) comprising administering to the individual an effective amount of a single chain recombinant placenta growth factor (PLGF) protein capable of binding to Flt-1, wherein the single chain PLGF comprises an amino acid sequence selected from SEQ ID NO: 1, 2, 3, 4, 5, 6, 7, 8, 9, 10, 11, 12, 13, 21 or 22.

2. The method of claim 1, wherein the single-chain PLGF protein is a monomeric PLGF protein.

3. The method of claim 2, wherein the monomeric PLGF protein comprises the amino acid sequence as shown in SEQ ID NO: 2.

4. The method of claim 1, wherein the single-chain PLGF protein comprises two fused monomers.

5. The method of claim 4, wherein at least one of the two fused monomers is a wild-type human PLGF monomer.

6. The method of claim 4, wherein the two monomers are fused via a linker.

7. The method of claim 6, wherein the linker is a peptide comprising 3-60 amino acids.

8. The method of claim 7, wherein the linker comprises a sequence at least 80% identical to
GSTSGSGKSSEGKG (SEQ ID NO: 14).

9. The method of claim 1, wherein the recombinant placenta growth factor (PLGF) protein is a dimeric PLGF protein comprising two monomers.

10. The method of claim 9, wherein at least one of the two monomers is a wild-type human PLGF monomer.

11. The method of claim 9, wherein the recombinant PLGF protein is the wild-type human PLGF protein (SEQ ID NO: 1).

12. The method of claim 1, wherein the recombinant PLGF protein is administered parenterally.

13. The method of claim 1, wherein the recombinant PLGF protein is delivered to one or more skeletal muscles selected from orbicularis oculi, ciliary, iris dilator, iris sphincter, auriculares, temporoparietalis, stapedius, tensor tympani, procerus, nasalis, dilator naris, depressor septi nasi, levator labii superioris alalaeque nasi, levator anguli oris, depressor anguli oris, orbicularis oris, buccinator zygomaticus major and minor, platysma, levator labii superioris, depressor labii inferioris, risorius, mentalis, corrugator supercilii, anconeus, pronator teres, supinator, brachialis, masseter, temporalis, medial pterygoid, lateral pterygoid, genioglos sus, styloglossus, palatoglos sus, hyoglos sus, digastric, stylohoid, mylohyoid, geniohyoid, omohyoid, sternohyoid, sternothyrioid, thyrohyoid, sternocleidomastoid, anterior scalene, middle scalene, posterior scalene, subclavius, pectoralis major, pectoralis minor rectus abdominis, external abdominal oblique, internal abdominal oblique, transversus abdominis, diaphragm, external intercostals, internal intercostals, serratus anterior, trapezius, levator scapulae, rhomboideus major, rhomboideus minor, latissimus dorsi, deltoid, subscapularis, supraspinatus, infraspinatus, teres major, teres minor, coracobrachialis, biceps brachii-long head, biceps brachii-short head, triceps brachii-long head, triceps brachii-lateral head, triceps brachii-medial head, anconeus, pronator teres, supinator, brachialis, brachioradialis, flexor carpi radialis, flexor carpi ulnaris, palmaris longus, extensor carpi ulnaris, ulnaris, extensor carpi radialis longus, extensor carpi, radialis brevis, extensor digitorum, extensor digiti minimi, erector spinae: cervicalis, erector spinae: spinalis, erector spinae: longissimus, erector spinae: iliocostalis, thenar, abductor pollicis brevis, flexor pollicis brevis, opponens pollicis, hypothenar, abductor digiti minimi, flexor digiti minimi brevis, opponens digiti minimi, palmar interossei, dorsal interossei, lumbricals, iliopsoas: psoas major, iliopsoas: iliacus, quadratus femoris, adductor longus, adductor brevis, adductor magnus, gracilis, sartorius, quadriceps femoris: rectus femoris, quadriceps femoris: vastus lateralis, quadriceps femoris: vastus medialis, quadriceps femoris: vastus intermedius, gastrocnemius, fibularis (peroneus) longus, soleus, gluteus maximus, gluteus medius, gluteus minimus, hamstring: biceps, femoris: long head, hamstrings: biceps, femoris: short head, hamstrings: semitendinosus, hamstrings: semimembranosus, tensor fasciae latae, pectineus, tibialis anterior, extensor digitorum longus, extensor hallucis longus, peroneus brevis, plantaris tibialis posterior, flexor halluces longus, extensor digitorum brevis, extensor halluces brevis, abductor halluces, flexor halluces brevis, abductor digiti minimi, flexor digiti minimi, opponens digiti minimi, extensor digitorum brevis, lumbricales of the foot, quadratus plantae, flexor accessories, flexor digitorum brevis, dorsal interossei, or plantar interossei.

14. The method of claim 1, wherein the single chain PLGF comprises an amino acid sequence of SEQ ID NO: 1, or variants thereof, having up to 3 amino acid substitutions at amino acids selected from Q26A, W29A, C59A, D71S, E72A, or L74R.

15. The method of claim 14, wherein the single chain PLGF has an alanine amino acid substitution at amino acid C59.

* * * * *